United States Patent
Carven et al.

(10) Patent No.: US 11,117,961 B2
(45) Date of Patent: *Sep. 14, 2021

(54) ANTIBODIES TO HUMAN PROGRAMMED DEATH RECEPTOR PD-1

(71) Applicant: Merck Sharp & Dohme B.V., Rahway, NJ (US)

(72) Inventors: Gregory John Carven, Maynard, MA (US); Hans van Eenennaam, Nijmegen (NL); Gradus Johannes Dulos, Elst (NL)

(73) Assignee: Merck Sharp & Dohme B.V.

( * ) Notice: Subject to any disclaimer, the term of this patent is extended or adjusted under 35 U.S.C. 154(b) by 514 days.

This patent is subject to a terminal disclaimer.

(21) Appl. No.: 15/810,892

(22) Filed: Nov. 13, 2017

(65) Prior Publication Data

US 2018/0111996 A1  Apr. 26, 2018

Related U.S. Application Data

(60) Division of application No. 14/576,448, filed on Dec. 19, 2014, now Pat. No. 9,834,605, which is a division of application No. 13/719,756, filed on Dec. 19, 2012, now Pat. No. 8,952,136, which is a continuation of application No. 12/663,950, filed as application No. PCT/US2008/007463 on Jun. 13, 2008, now Pat. No. 8,354,509.

(60) Provisional application No. 60/944,583, filed on Jun. 18, 2007.

(51) Int. Cl.
*A61K 39/395* (2006.01)
*C07K 16/28* (2006.01)
*G01N 33/574* (2006.01)
*G01N 33/68* (2006.01)

(52) U.S. Cl.
CPC ...... *C07K 16/2803* (2013.01); *C07K 16/2818* (2013.01); *G01N 33/57488* (2013.01); *G01N 33/6869* (2013.01); *C07K 2317/24* (2013.01); *C07K 2317/565* (2013.01); *C07K 2317/76* (2013.01); *C07K 2317/92* (2013.01); *G01N 2333/55* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,629,204 A | 5/1997 | Honjo et al. | |
| 5,698,520 A | 12/1997 | Honjo et al. | |
| 5,897,862 A | 4/1999 | Hardy et al. | |
| 6,632,927 B2 | 10/2003 | Adair et al. | |
| 6,808,710 B1 | 10/2004 | Wood et al. | |
| 7,029,674 B2 | 4/2006 | Carreno et al. | |
| 7,101,550 B2 | 9/2006 | Wood et al. | |
| 7,105,328 B2 | 9/2006 | Wood et al. | |
| 7,332,582 B2 | 2/2008 | Hardy et al. | |
| 7,488,802 B2 | 2/2009 | Collins et al. | |
| 7,521,051 B2 | 4/2009 | Collins et al. | |
| 7,524,498 B2 | 4/2009 | Hardy et al. | |
| 7,595,048 B2 | 9/2009 | Honjo et al. | |
| 7,858,746 B2 | 12/2010 | Honjo et al. | |
| 7,943,743 B2 | 5/2011 | Korman et al. | |
| 7,998,479 B2 | 8/2011 | Honjo et al. | |
| 8,008,449 B2 | 8/2011 | Korman et al. | |
| 8,168,757 B2 | 5/2012 | Finnefroch et al. | |
| 8,354,509 B2 | 1/2013 | Carven et al. | |
| 8,552,154 B2 | 10/2013 | Freeman et al. | |
| 8,652,465 B2 | 2/2014 | Freeman et al. | |
| 8,900,587 B2 | 12/2014 | Carven et al. | |
| 8,952,136 B2 | 2/2015 | Carven et al. | |
| 9,220,776 B2 * | 12/2015 | Sharma | A61K 9/0019 |
| 9,827,309 B2 * | 11/2017 | Strack | C07K 16/2818 |
| 9,834,605 B2 | 12/2017 | Carven et al. | |
| 9,907,849 B2 * | 3/2018 | Petit | A61K 39/39558 |
| 10,010,608 B2 * | 7/2018 | Hoos | A61K 31/519 |
| 10,188,729 B2 | 1/2019 | Danling et al. | |
| 10,188,730 B2 | 1/2019 | Liang | |
| 10,241,115 B2 * | 3/2019 | Pierce | G16H 20/40 |
| 10,251,922 B2 | 4/2019 | Palese et al. | |
| 10,335,388 B2 | 7/2019 | Josey et al. | |
| 10,570,202 B2 | 2/2020 | Martini et al. | |
| 10,618,958 B2 | 4/2020 | Williams et al. | |
| 10,647,771 B2 | 5/2020 | Yearley et al. | |
| 10,695,426 B2 | 6/2020 | Das-young et al. | |

(Continued)

FOREIGN PATENT DOCUMENTS

| | | |
|---|---|---|
| EP | 1591527 | 11/2005 |
| WO | 2000058363 A1 | 10/2000 |
| WO | 200114556 A1 | 2/2001 |
| WO | 200114557 A1 | 3/2001 |
| WO | 2002078731 A1 | 10/2002 |
| WO | 2002079499 A1 | 10/2002 |
| WO | 2003099196 A2 | 12/2003 |
| WO | 2004004771 A1 | 2/2004 |
| WO | 2004056875 A1 | 7/2004 |
| WO | 2006042237 A2 | 4/2006 |
| WO | 2006121168 A1 | 11/2006 |

(Continued)

OTHER PUBLICATIONS

Agata et al., Expression of the PD-1 antigen on the surface of stimulated mouse T and B lymphocytes, International Immunology, 1996, pp. 765-772, vol. 8, No. 5.

(Continued)

*Primary Examiner* — Ilia I Ouspenski
(74) *Attorney, Agent, or Firm* — Yingying Zeng; Alysia A. Finnegan

(57) ABSTRACT

Antibodies which block binding of hPD-1 to hPD-L1 or hPD-L2 and their variable region sequences are disclosed. A method of increasing the activity (or reducing downmodulation) of an immune cell through the PD-1 pathway is also disclosed.

57 Claims, 7 Drawing Sheets

Specification includes a Sequence Listing.

(56) References Cited

U.S. PATENT DOCUMENTS

| | | |
|---|---|---|
| 10,751,412 B2 | 8/2020 | Yu et al. |
| 10,766,957 B2 | 9/2020 | Williams et al. |
| 10,786,480 B2 | 9/2020 | Josey et al. |
| 10,899,840 B2 | 1/2021 | Davis et al. |
| 10,945,990 B2 | 3/2021 | Matsui et al. |
| 2003/0039653 A1 | 2/2003 | Chen et al. |
| 2006/0210567 A1 | 9/2006 | Collins et al. |
| 2007/0122378 A1 | 5/2007 | Freeman et al. |
| 2008/0311117 A1 | 12/2008 | Collins et al. |
| 2009/0076250 A1 | 3/2009 | Honjo et al. |
| 2013/0109843 A1 | 5/2013 | Carven et al. |
| 2018/0080938 A1 | 3/2018 | Dolled-filhart et al. |
| 2018/0092901 A1 | 4/2018 | Denker et al. |
| 2018/0148790 A1 | 5/2018 | Ayers et al. |
| 2018/0207266 A1 | 7/2018 | Danling et al. |
| 2018/0237524 A1 | 8/2018 | Reichert et al. |
| 2018/0298096 A1 | 10/2018 | Joyce-Shaikh et al. |
| 2018/0327848 A1 | 11/2018 | Ayers et al. |
| 2018/0333503 A1 | 11/2018 | Ruiz Soto |
| 2019/0091332 A1 | 3/2019 | Liang |
| 2019/0153093 A1 | 5/2019 | Meehl et al. |
| 2019/0160148 A1 | 5/2019 | Beckmann et al. |
| 2019/0183972 A1 | 6/2019 | Gaynor |
| 2019/0233518 A1 | 8/2019 | Fayadat-dilman et al. |
| 2019/0233523 A1 | 8/2019 | Gil et al. |
| 2019/0263927 A1 | 8/2019 | Olivo |
| 2019/0270802 A1 | 9/2019 | Shifrin et al. |
| 2019/0270812 A1 | 9/2019 | Leopold et al. |
| 2019/0300618 A1 | 10/2019 | Beebe et al. |
| 2019/0328762 A1 | 10/2019 | Cemerski et al. |
| 2019/0330340 A1 | 10/2019 | Bowman et al. |
| 2020/0055938 A1 | 2/2020 | Desai et al. |
| 2020/0061184 A1 | 2/2020 | Palese et al. |
| 2020/0115451 A1 | 4/2020 | Homet Moreno et al. |
| 2020/0147213 A1 | 5/2020 | Sharma et al. |
| 2020/0155521 A1 | 5/2020 | Schwartz et al. |
| 2020/0157220 A1 | 5/2020 | Punnonen et al. |
| 2020/0172492 A1 | 6/2020 | Cowley et al. |
| 2020/0216425 A1 | 7/2020 | Han et al. |
| 2020/0262919 A1 | 8/2020 | Zimmerman et al. |
| 2020/0262922 A1 | 8/2020 | Bhattacharya et al. |
| 2020/0270346 A1 | 8/2020 | Williams et al. |
| 2020/0276153 A1 | 9/2020 | Pinheiro et al. |
| 2020/0289493 A1 | 9/2020 | Bobilev et al. |
| 2020/0325228 A1 | 10/2020 | Martini et al. |
| 2020/0353022 A1 | 11/2020 | Gansert et al. |
| 2020/0354453 A1 | 11/2020 | De et al. |
| 2021/0008135 A1 | 1/2021 | Gansert et al. |
| 2021/0017276 A1 | 1/2021 | Williams et al. |
| 2021/0040127 A1 | 2/2021 | Achab et al. |
| 2021/0047408 A1 | 2/2021 | Lala et al. |
| 2021/0047409 A1 | 2/2021 | Lala et al. |
| 2021/0107904 A1 | 4/2021 | Larsen et al. |

FOREIGN PATENT DOCUMENTS

| | | |
|---|---|---|
| WO | 2007005874 A2 | 1/2007 |
| WO | 2007082154 A2 | 7/2007 |
| WO | 2008071447 A2 | 6/2008 |
| WO | 2009114335 A2 | 9/2009 |

OTHER PUBLICATIONS

Angal et al., A Single Amino Acid Substitution Abolishes the Heterogeneity of Chimeric Mouse/Human (IgG4) Antibody, Molecular Immunology, 1993, pp. 105-108, vol. 30(1).

Barber et al., Restoring function in exhausted CD8 T cells during chronic viral infection, Nature, 2006, pp. 682-687, vol. 439.

Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses, The Journal of Immunology, 2003, pp. 711-718, vol. 170.

Bishop et al., Lymphocyte responses to influenza and tetanus toxoid in vitro following intensive exercise and carbohydrate ingestion on consecutive days, Journal of Applied Phisiology, 2005, pp. 1327-1335, vol. 99, No. 4.

Blank et al., Blockade of PD-L1 (B7-H1) augments human tumor-specific T cell responses in vitro, Int. J. Cancer, 2006, pp. 317-327, vol. 119.

Blank et al., Contribution of the PD-L1/PD-1 pathway to T-cell exhaustion: an update on implications for chronic infections, Cancer Immunol. Immunother., 2007, pp. 739-745, vol. 56(5).

Brown et al., Expression and functional consequences of PD-1 ligands on natural APCS and tumors, THe FASEB Journal, 2001, pp. A345, vol. 15, No. 4.

Brown, Blockade of Programmed Death-1 Ligands on Dendritic Cells Enhances T Cell Activation and Cytokine Production, J. Immunol., 2003, pp. 1257-1266, vol. 170.

Chen et al., Role of the immune modulator programmed cell death-1 during development and apoptosis of mouse retinal ganglion cells, Invest Ophthalmol Vis Sci., 2009, pp. 4941-4948, vol. 50(10).

Chothia et al., Domain Association in Immunoglobulin Molecules—The Packing of Variable Domain, J. Mol. Biol., 1985, pp. 651-663, vol. 186.

Clackson et al., Making Antibody Fragments Using Phage Display Libraries, Nature, 1991, pp. 624-628, vol. 352.

Davies et al., Affinity improvement of single antibody VH domains: residues in all three hypervariable regions affect antigen binding, Immunotechnology, 1996, pp. 169-179, vol. 2.

Day et al., PD-1 expression on HIV-specific T cells is associated with T-cell exhaustion and disease progression, Nature, 2006, pp. 350-354, vol. 443.

Del-Rio et al., Antibody-mediated signaling through PD-1 costimulates T cells and enhances CD28-dependent proliferation, Eur. J. Immunol., 2005, pp. 3545-3560, vol. 25(12).

Dong et al., Tumor-associated B7-H1 promotes T-cell apoptosis: A potential mechanism of immune evasion, Nature Medicine, 2002, pp. 793-800, vol. 8(8).

Eiz-Vesper et al., Tetanus toxoid provides efficient T-cell help for the induction of HA-1H cytotoxic T cells, Transfusion, 2006, pp. 1210-1220, vol. 46(7).

Fleischer et al., Reactivity of Mouse T-Cell Hybridomas Expressing Human V beta Gene Segments with Staphylococcal and Streptococcal Superantigens, Infection and Immunity, 1996, pp. 987-994, vol. 64, No. 3.

Fleischer et al., T Cell Stimulation by Staphylococcal Enterotoxins, J. Exp. Medicine, 1988, pp. 1697-1707, vol. 167(5).

Foote et al., Antibody Framework Residues Affecting the Conformation of the Hypervariable Loops, J. Mol. Biol., 1992, pp. 487-499, vol. 224.

Freeman et al., Engagement of the PD-1 Immunoinhibitory Receptor by a Novel B7 Family Member Leads to Negative Regulation of Lymphocyte Activation, Blood, 2000, pp. 810a-811a, vol. 96, No. 11.

Freeman, et al., Engagement of the PD-1 Immunoinhibitory Receptor by a Novel B7 Family Member Leads to Negative Regulation of Lymphocyte Activation J. Exp. Med., 2000, pp. 1027-1034, vol. 192.

Ghitto et al., PD-L1 and PD-L2 differ in their molecular mechanisms of interaction with PD-1, International Immunology, 2010, pp. 651-660, vol. 22, No. 8

Hirano et al., Blockade of B7-H1 and PD-1 by Monoclonal Antibodies Potentiates Cancer Therapeutic Immunity, Cancer Research, 2005, pp. 1089-1096, vol. 65(3)

International Search Report of PCT/US2008/007463, dated Oct. 29, 2008.

Ishida et al., Induced expression of PD-1, a novel member of the immunoglobulin gene superfamily, upon programmed cell death, The EMBO Journal, 1992, pp. 3887-3895, vol. 11(11).

Isogawa et al., Oscillating CD8+ Cell Effector Functions after Antigen Recognition in the Liver, Immunity, 2005, pp. 53-63, vol. 23.

Iwai et al., Microanatomical localization of PD-1 in human tonsils, Immunology Letters, 2002, pp. 215-220, vol. 83, No. 3.

(56) References Cited

OTHER PUBLICATIONS

Iwai et al, PD-1 Inhibits Antiviral Immunity at the Effector Phase in the Liver, J. Exp. Med., 2003, pp. 39-50, vol. 198.
Iwai, Involvement of PD-L1 on tumor cells in the escape from host immune system and tumor immunotherapy by PD-L1 blockade, Proc. Natl. Acad. Sci. USA, 2002, pp. 12293-12297, vol. 99.
Kabilan et al., Detection of intracellular expression and secretion of interferon-gamma at the single-cell level after activation of human T cells with tetanus toxoid in vitro, Eur. J. Immunol., 1990, pp. 1085-1089, vol. 20.
Kanai et al., Blockade of B7-H1 Suppresses the Development of Chronic Intestinal Inflammation, The Journal of Immunology, 2003, pp. 4156-4163, vol. 171.
Keir et al., PD-1 and its ligands in T-cell immunity, Current Opinion in Immunology, 2007, pp. 309-314, vol. 19.
Keir et al., Programmed Death-1 (PD-1):PD-Ligand 1 Interactions Inhibit TCR-Mediated Positive Selection of Thymocytes, The Journal of Immunology, 2005, pp. 7372-7379, vol. 175.
Kim et al., Application of 13C NMR spectroscopy to paratope mapping for larger antigen-Fab complexes, FEBS Letters, 1994, pp. 246-250, vol. 346, Nos. 2-3.
Kohler et al., Continuous Cultures of Fused Cells Secreting Antibody of Predefined Specificity, Nature, 1975, pp. 495-497, vol. 256.
Liang et al., Regulation of PD-1, PD-L1, and PD-L2 expression during normal and autoimmune responses, Eur. J. Immunol., 2003, pp. 2706-2716, vol. 33.
Lin, The PD-1/PD-L1 complex resembles the antigen-binding Fv domains of antibodies and T cell receptors, Proc. Natl. Acad. Sci. USA, 2008, pp. 3011-3016, vol. 105.
Morea et al., Antibody Modeling: Implications for Engineering and Design, Methods, 2000, pp. 267-279, vol. 20.
Nishimura et al., Autoimmune Dilated Cardiomyopathy in PD-1 Receptor-Deficient Mice, Science, 2001, pp. 319-322, vol. 291.
Nishimura et al., Immunological studies on PD-1-deficient mice: implication of PD-1 as a negative regulator for B cell responses, International Immunology, 1998, pp. 1563-1572, vol. 10, No. 10.
Nomi et al., Clinical Significance and Therapeutic Potential of the Programmed Death-1 Ligand/Programmed Death-1 Pathway in Human Pancreatic Cancer, Clinical Cancer Research, 2007, pp. 2151-2157, vol. 13.
Okazaki, PD-1 and PD-1 ligands: from discovery to clinical application, Int. Immunol., 2007, pp. 813-824, vol. 19.
Panka et al., Variable region framework differences result in decreased or increased affinity of variant anti-digoxin antibodies, Proc. Natl. Acad. Sci. USA, 1988, pp. 3080-3084, vol. 85.
Parry et al., CTLA-4 and PD-1 Receptors Inhibit T-Cell Activation by Distinct Mechanisms, Molecular and Cellular Biology, 2005, pp. 9543-9553, vol. 25(21).
Rentero et al., Screening of Large Molecule Diversities by Phage Display, Chimia, 2011, pp. 843-8454, vol. 65.
Rudikoff, Single amino acid substitution altering antigen-binding specificity, Proc. Natl. Acad. Sci. USA, 1982, pp. 1979-1983, vol. 79.
Sakthivel et al., Programmed Death-1: From gene to protein in autoimmune human myasthenia gravis, Journal of Neuroimmunology, 2008, pp. 149-155, vol. 193.

Seko et al., Roles of programmed death-1 (PD-1)/PD-1 ligands pathway in the development of murine acute myocarditis caused by coxsackievirus B3, Cardiovascular Research, 2007, pp. 158-167, vol. 75.
Sequence Alignment, 2011, one page.
Strome et al., B7-H1 Blockade Augments Adoptive T-Cell Immunotherapy for Squamous Cell Cancinoma, Cancer Research, 2003, pp. 6501-6505, vol. 63.
Thompson et al., PD-1 Is Expressed by Tumor-Infiltrating Immune Cells and Is Associated with Poor Outcome for Patients with Renal Cell Carcinoma, Clinical Cancer Research, 2007, pp. 1757-1761, vol. 15.
Thompson et al., Tumor B7-H1 Is Associated with Poor Prognosis in Renal Cell Carcinoma Patients with Long-Term Follow-up, Cancer Res., 2006, pp. 3381-3385, vol. 66.
Trautmann et al., Upregulation of PD-1 expression on HIV-specific CD8 T cells leads to reversible immune dysfunction, Nature Medicine, 2006, pp. 1198-1202, vol. 12(10).
Tsushima et al., Predominant expression of B7-H1 and its immunoregulatory roles in oral squamous cell carcinoma, Oral Oncol., 2006, pp. 268-274, vol. 42.
Vaughan et al., Human Antibodies with Sub-nanomolar affinities isolated from a large non-immunized phage display library, Nature Biotechnology, 1996, pp. 309-314, vol. 14.
Waldmann T. A., Effective Cancer Therapy Through Immunomodulation, Annu. Rev. Med., 2006, pp. 65-81, vol. 57 (1).
Wang et al., Establishment of Nod-Pdcd1-/-mice as an efficient animal model of type I diabetes, Proc. Natl. Acad. Sci. USA, 2005, pp. 11823-11828, vol. 102.
Wang et al., In Vitro Characterization of the Anti-PD-1 Antibody Nivolumab, BMS-936558, and In Vivo Toxicology in Non-Human Primates, Cancer Immunol. Res., 2014, pp. 846-856, vol. 2.
Wintterle et al., Expression of the B7-Related Molecule B7-H1 by Glioma Cells: A Potential Mechanism of Immune Paralysis, Cancer Res., 2003, pp. 7462-7467, vol. 63.
Wong et al., Programmed death-1 blockade enhances expansion and functional capacity of human melanoma antigen-specific CTLs, International Immunology, 2007, pp. 1223-1234, vol. 19(10).
Written Opinion of PCT/US2008/007463 dated Dec. 18, 2009.
Youngnak et al., Differential binding properties of B7-H1 and B7-DC to programmed death-1, Biochemical and Biophysical Research Communications, 2003, pp. 672-677, vol. 307.
Zehavi-Willner et al., The mitogenic activity of staphylococcal enterotoxin B (SEB): a monovalent T cell mitogen that stimulates cytolytic T lymphocytes but cannot mediate their lytic interaction, J Immunol., 1986, pp. 2682-2687, vol. 137(8).
Zhang et al., Structural and Functional Analysis of the Costimulatory Receptor Programmed Death-1, Immunity, 2004, pp. 337-347, vol. 20.
Zuberek et al., In vitro and In vivo Expression Regulation of PD-1 and PD-L1 in murine tumor models, Blood, 2001, pp. 25a, vol. 98, No. 11, Part 1 of 2 parts.
Zuberek et al., The role of in vivo PD-1/PD-L1 interactions in syngenic and allogeneic antitumor responses in murine tumor models, Blood, 2001, pp. 42b, vol. 98, No. 11, Part 2 of 2 parts.
U.S. Appl. No. 14/576,448, filed Dec. 19, 2014.
U.S. Appl. No. 13/719,759, filed Dec. 19, 2012.
U.S. Appl. No. 12/663,950, filed Jun. 21, 2010.

* cited by examiner

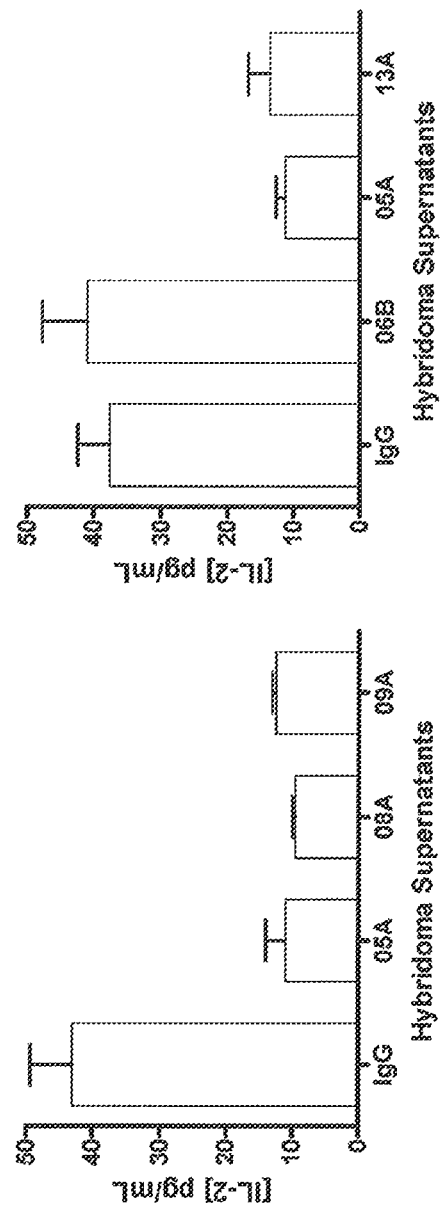

SEQUENCE LISTING

<160> NUMBER OF SEQ ID NOS: 38

<210> SEQ ID NO 1
<211> LENGTH: 435
<212> TYPE: DNA
<213> ORGANISM: Artificial Sequence
<220> FEATURE:
<223> OTHER INFORMATION: hPD-1.08A heavy chain variable region

<400> SEQUENCE: 1

| | | | | | | |
|---|---|---|---|---|---|---|
| atgrgatgga | gctgtatcat | kctcttttg | gtagcaacag | ctacaggtgt | ccactcccag | 60 |
| gtccaactgc | agcagcctgg | ggctgaactg | gtgaagcctg | ggcttcagt | gaagttgtcc | 120 |
| tgcaaggcct | ctggctacac | cttcaccagt | tattatctgt | actggatgaa | acagaggcct | 180 |
| ggacaaggcc | ttgagtggat | tggggggtt | aatcctagta | atggtggtac | taacttcagt | 240 |
| gagaagttca | agagcaaggc | cacactgact | gtagacaaat | cctccagcac | agcctacatg | 300 |
| caactcagca | gcctgacatc | tgaggactct | gcggtctatt | actgtacaag | aagggattct | 360 |
| aactacgacg | gggctttga | ctactggggc | caaggcacta | ctctcacagt | ctcctcagcc | 420 |
| aaaacgacac | cccca | | | | | 435 |

<210> SEQ ID NO 2
<211> LENGTH: 453
<212> TYPE: DNA
<213> ORGANISM: Artificial Sequence
<220> FEATURE:
<223> OTHER INFORMATION: hPD-1.08A light chain variable region

<400> SEQUENCE: 2

| | | | | | | |
|---|---|---|---|---|---|---|
| atggagacag | acacactcct | gctatgggta | ctgctgctct | ggttccagg | ttccactggt | 60 |
| gacattgtgc | tgacacagtc | tcctacttcc | ttagctgtat | ctctggggca | gagggccacc | 120 |
| atctcatgca | gggccagcaa | aagtgtcagt | acatctggct | ttagttattt | gcactggtac | 180 |
| caacagaaac | caggacagcc | acccaaactc | ctcatctttc | ttgcatccaa | cctagagtct | 240 |
| ggggtccctg | ccaggttcag | tggcagtggg | tctgggacag | acttcaccct | caacatccat | 300 |
| cctgtggagg | aggaggacgc | tgcaacctat | tattgtcagc | acagttggga | gcttccgctc | 360 |
| acgttcggtg | ctgggaccaa | gctggagctg | aaacgggctg | atgctgcacc | aactgtatcc | 420 |
| atcttcccac | catccagtaa | gcttgggaag | ggc | | | 453 |

<210> SEQ ID NO 3
<211> LENGTH: 464
<212> TYPE: DNA
<213> ORGANISM: Artificial Sequence
<220> FEATURE:
<223> OTHER INFORMATION: hPD-1.09A heavy chain variable region

<400> SEQUENCE: 3

| | | | | | | |
|---|---|---|---|---|---|---|
| atgraatgca | gctgggttat | yctcttttg | gtagcaacag | ctacaggtgt | ccactcccag | 60 |
| gtccaactgc | agcagcctgg | ggctgaactg | gtgaagcctg | ggacttcagt | gaagttgtcc | 120 |
| tgcaaggctt | ctggctacac | cttcaccaac | tactatatgt | actgggtgaa | gcagaggcct | 180 |
| ggacaaggcc | ttgagtggat | tgggggatt | aatcctagca | atggtggtac | taacttcaat | 240 |
| gagaagttca | agaacaaggc | cacactgact | gtagacagtt | cctccagcac | aacctacatg | 300 |
| caactcagca | gcctgacatc | tgaggactct | gcggtctatt | actgtacaag | aagggattat | 360 |
| aggttcgaca | tggctttga | ctactggggc | caaggcacca | ctctcacagt | ctcctcagcc | 420 |
| aaaacgacac | cccatccgt | ytatcccbtg | gcccctggaa | gctt | | 464 |

<210> SEQ ID NO 4
<211> LENGTH: 438
<212> TYPE: DNA
<213> ORGANISM: Artificial Sequence
<220> FEATURE:
<223> OTHER INFORMATION: hPD-1.09A light chain variable region

<400> SEQUENCE: 4

```
atggagwcag acacactsct gytatgggta ctgctgctct gggttccagg ttccactggc      60
gacattgtgc tgacacagtc tcctgcttcc ttagctgtat ctctgggaca gagggccgcc     120
atctcatgca gggccagcaa aggtgtcagt acatctggct atagttattt gcactggtac     180
caacagaaac caggacagtc acccaaactc ctcatctatc ttgcatccta cctagaatct     240
ggggtccctg ccaggttcag tggcagtggg tctgggacag acttcaccct caacatccat     300
cctgtggagg aggaggatgc tgcaacctat tactgtcagc acagtaggga ccttccgctc     360
acgttcggta ctgggaccaa gctggagctg aaacgggctg atgctgcacc aactgtatcc     420
atcttcccac catccagt                                                   438
```

<210> SEQ ID NO 5
<211> LENGTH: 122
<212> TYPE: PRT
<213> ORGANISM: Artificial Sequence
<220> FEATURE:
<223> OTHER INFORMATION: hPD-1.08A heavy chain variable region

<400> SEQUENCE: 5

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Met Lys Gln Arg Pro Gly Gln Gly Leu Glu Trp Ile
        35                  40                  45

Gly Gly Val Asn Pro Ser Asn Gly Gly Thr Asn Phe Ser Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Leu Thr Val Ser Ser Ala Lys
        115                 120
```

<210> SEQ ID NO 6
<211> LENGTH: 111
<212> TYPE: PRT
<213> ORGANISM: Artificial Sequence
<220> FEATURE:
<223> OTHER INFORMATION: hPD-1.08A light chain variable region

<400> SEQUENCE: 6

```
Asp Ile Val Leu Thr Gln Ser Pro Thr Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Phe Ser Tyr Leu His Trp Tyr Gln Gln Lys Pro Gly Gln Pro Pro
        35                  40                  45
```

```
Lys Leu Leu Ile Phe Leu Ala Ser Asn Leu Glu Ser Gly Val Pro Ala
         50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Trp
                 85                  90                  95

Glu Leu Pro Leu Thr Phe Gly Ala Gly Thr Lys Leu Glu Leu Lys
            100                 105                 110

<210> SEQ ID NO 7
<211> LENGTH: 122
<212> TYPE: PRT
<213> ORGANISM: Artificial Sequence
<220> FEATURE:
<223> OTHER INFORMATION: hPD-1.09A heavy chain variable region

<400> SEQUENCE: 7

Gln Val Gln Leu Gln Gln Pro Gly Ala Glu Leu Val Lys Pro Gly Thr
 1               5                  10                  15

Ser Val Lys Leu Ser Cys Lys Ala Ser Gly Tyr Thr Phe Thr Asn Tyr
             20                  25                  30

Tyr Met Tyr Trp Val Lys Gln Arg Pro Gly Gln Gly Leu Glu Trp Ile
         35                  40                  45

Gly Gly Ile Asn Pro Ser Asn Gly Gly Thr Asn Phe Asn Glu Lys Phe
     50                  55                  60

Lys Asn Lys Ala Thr Leu Thr Val Asp Ser Ser Ser Thr Thr Tyr
 65                  70                  75                  80

Met Gln Leu Ser Ser Leu Thr Ser Glu Asp Ser Ala Val Tyr Tyr Cys
                 85                  90                  95

Thr Arg Arg Asp Tyr Arg Phe Asp Met Gly Phe Asp Tyr Trp Gly Gln
            100                 105                 110

Gly Thr Thr Leu Thr Val Ser Ser Ala Lys
        115                 120

<210> SEQ ID NO 8
<211> LENGTH: 111
<212> TYPE: PRT
<213> ORGANISM: Artificial Sequence
<220> FEATURE:
<223> OTHER INFORMATION: hPD-1.09A light chain variable region

<400> SEQUENCE: 8

Asp Ile Val Leu Thr Gln Ser Pro Ala Ser Leu Ala Val Ser Leu Gly
 1               5                  10                  15

Gln Arg Ala Ala Ile Ser Cys Arg Ala Ser Lys Gly Val Ser Thr Ser
             20                  25                  30

Gly Tyr Ser Tyr Leu His Trp Tyr Gln Gln Lys Pro Gly Gln Ser Pro
         35                  40                  45

Lys Leu Leu Ile Tyr Leu Ala Ser Tyr Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Asp Leu Pro Leu Thr Phe Gly Thr Gly Thr Lys Leu Glu Leu Lys
            100                 105                 110
```

```
<210> SEQ ID NO 9
<211> LENGTH: 15
<212> TYPE: PRT
<213> ORGANISM: Artificial Sequence
<220> FEATURE:
<223> OTHER INFORMATION: hPD-1.08A light chain CDR1

<400> SEQUENCE: 9

Arg Ala Ser Lys Ser Val Ser Thr Ser Gly Phe Ser Tyr Leu His
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: hPD-1.08A light chain CDR2

<400> SEQUENCE: 10

Leu Ala Ser Asn Leu Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: hPD-1-08A light chain CDR3

<400> SEQUENCE: 11

Gln His Ser Trp Glu Leu Pro Leu Thr
1               5

<210> SEQ ID NO 12
<211> LENGTH: 5
<212> TYPE: PRT
<213> ORGANISM: Artificial Sequence
<220> FEATURE:
<223> OTHER INFORMATION: hPD-1.08A heavy chain CDR1

<400> SEQUENCE: 12

Ser Tyr Tyr Leu Tyr
1               5

<210> SEQ ID NO 13
<211> LENGTH: 17
<212> TYPE: PRT
<213> ORGANISM: Artificial Sequence
<220> FEATURE:
<223> OTHER INFORMATION: hPD-1.08A heavy chain CDR2

<400> SEQUENCE: 13

Gly Val Asn Pro Ser Asn Gly Gly Thr Asn Phe Ser Glu Lys Phe Lys
1               5                   10                  15

Ser

<210> SEQ ID NO 14
<211> LENGTH: 11
<212> TYPE: PRT
<213> ORGANISM: Artificial Sequence
<220> FEATURE:
<223> OTHER INFORMATION: hPD-1.08A heavy chain CDR3

<400> SEQUENCE: 14

Arg Asp Ser Asn Tyr Asp Gly Gly Phe Asp Tyr
1               5                   10
```

<210> SEQ ID NO 15
<211> LENGTH: 15
<212> TYPE: PRT
<213> ORGANISM: Artificial Sequence
<220> FEATURE:
<223> OTHER INFORMATION: hPD-1.09A light chain CDR1

<400> SEQUENCE: 15

```
Arg Ala Ser Lys Gly Val Ser Thr Ser Gly Tyr Ser Tyr Leu His
1               5                   10                  15
```

<210> SEQ ID NO 16
<211> LENGTH: 7
<212> TYPE: PRT
<213> ORGANISM: Artificial Sequence
<220> FEATURE:
<223> OTHER INFORMATION: hPD-1.09A light chain CDR2

<400> SEQUENCE: 16

```
Leu Ala Ser Tyr Leu Glu Ser
1               5
```

<210> SEQ ID NO 17
<211> LENGTH: 9
<212> TYPE: PRT
<213> ORGANISM: Artificial Sequence
<220> FEATURE:
<223> OTHER INFORMATION: hPD-1.09A light chain CDR3

<400> SEQUENCE: 17

```
Gln His Ser Arg Asp Leu Pro Leu Thr
1               5
```

<210> SEQ ID NO 18
<211> LENGTH: 5
<212> TYPE: PRT
<213> ORGANISM: Artificial Sequence
<220> FEATURE:
<223> OTHER INFORMATION: hPD-1.09A heavy chain CDR1

<400> SEQUENCE: 18

```
Asn Tyr Tyr Met Tyr
1               5
```

<210> SEQ ID NO 19
<211> LENGTH: 17
<212> TYPE: PRT
<213> ORGANISM: Artificial Sequence
<220> FEATURE:
<223> OTHER INFORMATION: hPD-1.09A heavy chain CDR2

<400> SEQUENCE: 19

```
Gly Ile Asn Pro Ser Asn Gly Gly Thr Asn Phe Asn Glu Lys Phe Lys
1               5                   10                  15

Asn
```

<210> SEQ ID NO 20
<211> LENGTH: 11
<212> TYPE: PRT
<213> ORGANISM: Artificial Sequence
<220> FEATURE:
<223> OTHER INFORMATION: hPD-1.09A heavy chain CDR3

<400> SEQUENCE: 20

```
Arg Asp Tyr Arg Phe Asp Met Gly Phe Asp Tyr
1               5                   10
```

<210> SEQ ID NO 21
<211> LENGTH: 417
<212> TYPE: DNA
<213> ORGANISM: Artificial Sequence
<220> FEATURE:
<223> OTHER INFORMATION: 109A-H heavy chain variable region
<220> FEATURE:
<221> NAME/KEY: sig_peptide
<222> LOCATION: (1)..(57)

<400> SEQUENCE: 21

```
atggactgga cctggagcat ccttttcttg gtggcagcac caacaggagc ccactcccaa    60
gtgcagctgg tgcagtctgg agttgaagtg aagaagcccg ggcctcagt gaaggtctcc   120
tgcaaggctt ctggctacac ctttaccaac tactatatgt actgggtgcg acaggcccct   180
ggacaagggc ttgagtggat gggagggatt aatcctagca atggtggtac taacttcaat   240
gagaagttca agaacagagt caccttgacc acagactcat ccacgaccac agcctacatg   300
gaactgaaga gcctgcaatt tgacgacacg gccgtttatt actgtgcgag aagggattat   360
aggttcgaca tgggctttga ctactggggc caagggacca cggtcaccgt ctcgagc     417
```

<210> SEQ ID NO 22
<211> LENGTH: 417
<212> TYPE: DNA
<213> ORGANISM: Artificial Sequence
<220> FEATURE:
<223> OTHER INFORMATION: Codon optimized 109A-H heavy chain variable
      region
<220> FEATURE:
<221> NAME/KEY: sig_peptide
<222> LOCATION: (1)..(57)

<400> SEQUENCE: 22

```
atggactgga cctggtctat cctgttcctg gtggccgctc ctaccggcgc tcactcccag    60
gtgcagctgg tgcagtccgg cgtggaggtg aagaagcctg cgcctccgt caaggtgtcc   120
tgcaaggcct ccggctacac cttcaccaac tactacatgt actgggtgcg caggctccc   180
ggccagggac tggagtggat gggcggcatc aaccccttcc acggcggcac caacttcaac   240
gagaagttca gaaccgggt gaccctgacc accgactcct ccaccaccac cgcctacatg   300
gagctgaagt ccctgcagtt cgacgacacc gccgtgtact actgcgccag cgggactac   360
cggttcgaca tgggcttcga ctactggggc cagggcacca ccgtgaccgt gtcctcc     417
```

<210> SEQ ID NO 23
<211> LENGTH: 1398
<212> TYPE: DNA
<213> ORGANISM: Artificial Sequence
<220> FEATURE:
<223> OTHER INFORMATION: Codon optimized 409A-H heavy chain full length
<220> FEATURE:
<221> NAME/KEY: sig_peptide
<222> LOCATION: (1)..(57)

<400> SEQUENCE: 23

```
atggccgtgc tgggcctgct gttctgcctg gtgaccttcc cttcctgcgt gctgtcccag    60
gtgcagctgg tgcagtccgg cgtggaggtg aagaagcctg cgcctccgt caaggtgtcc   120
tgtaaggcct ccggctacac cttcaccaac tactacatgt actgggtgcg caggcccca   180
ggccagggac tggagtggat gggcggcatc aaccccttcc acggcggcac caacttcaac   240
gagaagttca gaaccgggt gaccctgacc accgactcct ccaccacaac cgcctacatg   300
```

```
gaactgaagt ccctgcagtt cgacgacacc gccgtgtact actgcgccag gcgggactac      360
cggttcgaca tgggcttcga ctactggggc cagggcacca ccgtgaccgt gtcctccgct      420
agcaccaagg gcccttccgt gttccctctg gccccttgct cccggtccac ctccgagtcc      480
accgccgctc tgggctgtct ggtgaaggac tacttccctg agcctgtgac cgtgagctgg      540
aactctggcg ccctgacctc cggcgtgcac accttccctg ccgtgctgca gtcctccggc      600
ctgtactccc tgtcctccgt ggtgaccgtg ccttcctcct ccctgggcac caagacctac      660
acctgcaacg tggaccacaa gccttccaac accaaggtgg acaagcgggt ggagtccaag      720
tacggccctc cttgcccctcc ctgccctgcc ctgagttcc tgggcggacc ctccgtgttc      780
ctgttccctc ctaagcctaa ggacaccctg atgatctccc ggaccctga ggtgacctgc       840 gtggtggtgg acgtgtccca ggaagatcct gaggtccagt tcaattggta cgtggatggc      900
gtggaggtgc acaacgccaa gaccaagcct cgggaggaac agttcaactc cacctaccgg      960
gtggtgtctg tgctgaccgt gctgcaccag gactggctga acggcaagga atacaagtgc     1020
aaggtcagca caagggcct gccctcctcc atcgagaaaa ccatctccaa ggccaagggc      1080
cagcctcgcg agcctcaggt gtacaccctg cctcctagcc aggaagagat gaccaagaat     1140
caggtgtccc tgacatgcct ggtgaagggc ttctaccctt ccgatatcgc cgtggagtgg     1200
gagagcaacg gccagccaga gaacaactac aagaccaccc ctcctgtgct ggactccgac     1260
ggctccttct cctgtactc caggctgacc gtggacaagt cccggtggca ggaaggcaac      1320
gtcttttcct gctccgtgat gcacgaggcc ctgcacaacc actacaccca gaagtccctg     1380
tccctgtctc tgggcaag                                                   1398

<210> SEQ ID NO 24
<211> LENGTH: 393
<212> TYPE: DNA
<213> ORGANISM: Artificial Sequence
<220> FEATURE:
<223> OTHER INFORMATION: K09A-L-11 light chain variable region
<220> FEATURE:
<221> NAME/KEY: sig_peptide
<222> LOCATION: (1)..(60)

<400> SEQUENCE: 24
atggaagccc cagctcagct tctcttcctc ctgctactct ggctcccaga taccaccgga       60
gaaattgtgt tgacacagtc tccagccacc ctgtctttgt ctccagggga aagagccacc      120
ctctcctgca gggccagcaa aggtgtcagt acatctggct atagttattt gcactggtat      180
caacagaaac ctggccaggc tcccaggctc ctcatctatc ttgcatccta cctagaatct      240
ggcgtcccag ccaggttcag tggtagtggg tctgggacag acttcactct caccatcagc      300
agcctagagc ctgaagattt tgcagtttat tactgtcagc acagcaggga ccttccgctc      360
acgttcggcg agggaccaa agtggagatc aaa                                   393

<210> SEQ ID NO 25
<211> LENGTH: 393
<212> TYPE: DNA
<213> ORGANISM: Artificial Sequence
<220> FEATURE:
<223> OTHER INFORMATION: K09A-L-16 light chain variable region
<220> FEATURE:
<221> NAME/KEY: sig_peptide
<222> LOCATION: (1)..(60)

<400> SEQUENCE: 25
atggaaaccc cagcgcagct tctcttcctc ctgctactct ggctcccaga taccaccgga       60
```

```
gaaattgtgc tgactcagtc tccactctcc ctgcccgtca cccctggaga gccggcctcc    120
atctcctgca gggccagcaa aggtgtcagt acatctggct atagttattt gcattggtac    180
ctccagaagc cagggcagtc tccacagctc ctgatctatc ttgcatccta cctagaatct    240
ggggtccctg acaggttcag tggcagtgga tcaggcacag attttacact gaaaatcagc    300
agagtggagg ctgaggatgt tggggtttat tactgccagc atagtaggga ccttccgctc    360
acgtttggcc aggggaccaa gctggagatc aaa                                 393
```

<210> SEQ ID NO 26
<211> LENGTH: 393
<212> TYPE: DNA
<213> ORGANISM: Artificial Sequence
<220> FEATURE:
<223> OTHER INFORMATION: K09A-L-17 light chain variable region
<220> FEATURE:
<221> NAME/KEY: sig_peptide
<222> LOCATION: (1)..(60)

<400> SEQUENCE: 26

```
atgaggctcc ctgctcagct cctggggctg ctaatgctct gggtctctgg atccagtggg     60
gatattgtga tgacccagac tccactctcc ctgcccgtca cccctggaga gccggcctcc    120
atctcctgca gggccagcaa aggtgtcagt acatctggct atagttattt gcattggtat    180
ctgcagaagc cagggcagtc tccacagctc ctgatctatc ttgcatccta cctagaatct    240
ggagtcccag acaggttcag tggcagtggg tcaggcactg ctttcacact gaaaatcagc    300
agggtggagg ctgaggatgt tgactttat tactgccagc atagtaggga ccttccgctc    360
acgtttggcc aggggaccaa gctggagatc aaa                                 393
```

<210> SEQ ID NO 27
<211> LENGTH: 390
<212> TYPE: DNA
<213> ORGANISM: Artificial Sequence
<220> FEATURE:
<223> OTHER INFORMATION: Codon optimized K09A-L-11 light chain variable
      region
<220> FEATURE:
<221> NAME/KEY: sig_peptide
<222> LOCATION: (1)..(57)

<400> SEQUENCE: 27

```
atggcccctg tgcagctgct gggcctgctg gtgctgttcc tgcctgccat gcggtgcgag     60
atcgtgctga cccagtcccc tgccaccctg tccctgagcc ctggcgagcg gctaccctg    120 agctgcagag cctccaaggg cgtgtccacc tccggctact cctacctgca ctggtatcag    180
cagaagccag gccaggcccc tcggctgctg atctacctgg cctcctacct ggagtccggc    240
gtgcctgccc ggttctccgg ctccggaagc ggcaccgact cacccttgac catctcctcc    300
ctggagcctg aggacttcgc cgtgtactac tgccagcact cccgggacct gcctctgacc    360
tttggcggcg gaacaaaggt ggagatcaag                                     390
```

<210> SEQ ID NO 28
<211> LENGTH: 390
<212> TYPE: DNA
<213> ORGANISM: Artificial Sequence
<220> FEATURE:
<223> OTHER INFORMATION: Codon optimized K09A-L-16 light chain variable
      region
<220> FEATURE:
<221> NAME/KEY: sig_peptide
<222> LOCATION: (1)..(57)

<400> SEQUENCE: 28

```
atggccctg tgcagctgct gggcctgctg gtgctgttcc tgcctgccat gcggtgcgag    60
atcgtgctga cccagtcccc tctgtccctg cctgtgaccc ctggcgagcc tgcctccatc   120
tcctgccggg cctccaaggg cgtgtccacc tccggctact cctacctgca ctggtatctg   180
cagaagcctg gccagtcccc ccagctgctg atctacctgg cctcctacct ggagtccggc   240
gtgcctgacc ggttctccgg ctccggcagc ggcaccgact tcaccctgaa gatctcccgg   300
gtggaggccg aggacgtggg cgtgtactac tgccagcact cccgggacct gcctctgacc   360
ttcggccagg gcaccaagct ggagatcaag                                    390
```

<210> SEQ ID NO 29
<211> LENGTH: 390
<212> TYPE: DNA
<213> ORGANISM: Artificial Sequence
<220> FEATURE:
<223> OTHER INFORMATION: Codon optimized K09A-L-17 light chain variable
      region
<220> FEATURE:
<221> NAME/KEY: sig_peptide
<222> LOCATION: (1)..(57)

<400> SEQUENCE: 29

```
atggccctg tgcagctgct gggcctgctg gtgctgttcc tgcctgccat gcggtgcgac    60
atcgtgatga cccagacccc tctgtccctg cctgtgaccc ctggcgagcc tgcctccatc   120
tcctgccggg cctccaaggg cgtgtccacc tccggctact cctacctgca ctggtatctg   180
cagaagcctg gccagtcccc tcagctgctg atctacctgg cctcctacct ggagtccggc   240
gtgcctgacc ggttctccgg ctccggaagc ggcaccgctt taccctgaa gatctcccaga   300
gtggaggccg aggacgtggg cctgtactac tgccagcact cccgggacct gcctctgacc   360
ttcggccagg gcaccaagct ggagatcaag                                    390
```

<210> SEQ ID NO 30
<211> LENGTH: 139
<212> TYPE: PRT
<213> ORGANISM: Artificial Sequence
<220> FEATURE:
<223> OTHER INFORMATION: 109A-H heavy chain variable region
<220> FEATURE:
<221> NAME/KEY: sig_peptide
<222> LOCATION: (1)..(19)

<400> SEQUENCE: 30

```
Met Asp Trp Thr Trp Ser Ile Leu Phe Leu Val Ala Ala Pro Thr Gly
1               5                   10                  15
Ala His Ser Gln Val Gln Leu Val Gln Ser Gly Val Glu Val Lys Lys
                20                  25                  30
Pro Gly Ala Ser Val Lys Val Ser Cys Lys Ala Ser Gly Tyr Thr Phe
            35                  40                  45
Thr Asn Tyr Tyr Met Tyr Trp Val Arg Gln Ala Pro Gly Gln Gly Leu
        50                  55                  60
Glu Trp Met Gly Gly Ile Asn Pro Ser Asn Gly Gly Thr Asn Phe Asn
65                  70                  75                  80
Glu Lys Phe Lys Asn Arg Val Thr Leu Thr Thr Asp Ser Ser Thr Thr
                85                  90                  95
Thr Ala Tyr Met Glu Leu Lys Ser Leu Gln Phe Asp Asp Thr Ala Val
            100                 105                 110
```

```
Tyr Tyr Cys Ala Arg Arg Asp Tyr Arg Phe Asp Met Gly Phe Asp Tyr
            115                 120                 125

Trp Gly Gln Gly Thr Thr Val Thr Val Ser Ser
        130                 135
```

<210> SEQ ID NO 31
<211> LENGTH: 466
<212> TYPE: PRT
<213> ORGANISM: Artificial Sequence
<220> FEATURE:
<223> OTHER INFORMATION: 409A-H heavy chain full length
<220> FEATURE:
<221> NAME/KEY: sig_peptide
<222> LOCATION: (1)..(19)

<400> SEQUENCE: 31

```
Met Ala Val Leu Gly Leu Leu Phe Cys Leu Val Thr Phe Pro Ser Cys
1               5                   10                  15

Val Leu Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320
```

```
Val Val Ser Val Leu Thr Val Leu His Gln Asp Trp Leu Asn Gly Lys
            325                 330                 335

Glu Tyr Lys Cys Lys Val Ser Asn Lys Gly Leu Pro Ser Ser Ile Glu
        340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 32
<211> LENGTH: 130
<212> TYPE: PRT
<213> ORGANISM: Artificial Sequence
<220> FEATURE:
<223> OTHER INFORMATION: K09A-L-11 light chain variable region
<220> FEATURE:
<221> NAME/KEY: sig_peptide
<222> LOCATION: (1)..(19)

<400> SEQUENCE: 32

Met Ala Pro Val Gln Leu Leu Gly Leu Leu Val Leu Phe Leu Pro Ala
1               5                   10                  15

Met Arg Cys Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

His Ser Arg Asp Leu Pro Leu Thr Phe Gly Gly Gly Thr Lys Val Glu
        115                 120                 125

Ile Lys
    130

<210> SEQ ID NO 33
<211> LENGTH: 130
<212> TYPE: PRT
<213> ORGANISM: Artificial Sequence
<220> FEATURE:
<223> OTHER INFORMATION: K09A-L-16 light chain variable region
<220> FEATURE:
<221> NAME/KEY: sig_peptide
```

<222> LOCATION: (1)..(19)

<400> SEQUENCE: 33

Met Ala Pro Val Gln Leu Leu Gly Leu Leu Val Leu Phe Leu Pro Ala
1               5                   10                  15

Met Arg Cys Glu Ile Val Leu Thr Gln Ser Pro Leu Ser Leu Pro Val
            20                  25                  30

Thr Pro Gly Glu Pro Ala Ser Ile Ser Cys Arg Ala Ser Lys Gly Val
        35                  40                  45

Ser Thr Ser Gly Tyr Ser Tyr Leu His Trp Tyr Leu Gln Lys Pro Gly
    50                  55                  60

Gln Ser Pro Gln Leu Leu Ile Tyr Leu Ala Ser Tyr Leu Glu Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Val Gly Val Tyr Tyr Cys Gln
            100                 105                 110

His Ser Arg Asp Leu Pro Leu Thr Phe Gly Gln Gly Thr Lys Leu Glu
        115                 120                 125

Ile Lys
    130

<210> SEQ ID NO 34
<211> LENGTH: 130
<212> TYPE: PRT
<213> ORGANISM: Artificial Sequence
<220> FEATURE:
<223> OTHER INFORMATION: K09A-L-17 light chain variable region
<220> FEATURE:
<221> NAME/KEY: sig_peptide
<222> LOCATION: (1)..(19)

<400> SEQUENCE: 34

Met Ala Pro Val Gln Leu Leu Gly Leu Leu Val Leu Phe Leu Pro Ala
1               5                   10                  15

Met Arg Cys Asp Ile Val Met Thr Gln Thr Pro Leu Ser Leu Pro Val
            20                  25                  30

Thr Pro Gly Glu Pro Ala Ser Ile Ser Cys Arg Ala Ser Lys Gly Val
        35                  40                  45

Ser Thr Ser Gly Tyr Ser Tyr Leu His Trp Tyr Leu Gln Lys Pro Gly
    50                  55                  60

Gln Ser Pro Gln Leu Leu Ile Tyr Leu Ala Ser Tyr Leu Glu Ser Gly
65                  70                  75                  80

Val Pro Asp Arg Phe Ser Gly Ser Gly Ser Gly Thr Ala Phe Thr Leu
                85                  90                  95

Lys Ile Ser Arg Val Glu Ala Glu Asp Val Gly Leu Tyr Tyr Cys Gln
            100                 105                 110

His Ser Arg Asp Leu Pro Leu Thr Phe Gly Gln Gly Thr Lys Leu Glu
        115                 120                 125

Ile Lys
    130

<210> SEQ ID NO 35
<211> LENGTH: 469
<212> TYPE: PRT
<213> ORGANISM: Artificial Sequence
<220> FEATURE:
<223> OTHER INFORMATION: 109A-H heavy chain full length
<220> FEATURE:

```
<221> NAME/KEY: sig_peptide
<222> LOCATION: (1)..(19)

<400> SEQUENCE: 35

Met Ala Val Leu Gly Leu Leu Phe Cys Leu Val Thr Phe Pro Ser Cys
 1               5                  10                  15

Val Leu Ser Gln Val Gln Leu Val Gln Ser Gly Val Glu Val Lys Lys
            20                  25                  30

Pro Gly Ala Ser Val Lys Val Ser Cys Lys Ala Ser Gly Tyr Thr Phe
        35                  40                  45

Thr Asn Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Asn Arg Val Thr Leu Thr Thr Asp Ser Ser Thr Thr
                85                  90                  95

Thr Ala Tyr Met Glu Leu Lys Ser Leu Gln Phe Asp Asp Thr Ala Val
            100                 105                 110

Tyr Tyr Cys Ala Arg Arg Asp Tyr Arg Phe Asp Met Gly Phe Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400
```

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 36
<211> LENGTH: 237
<212> TYPE: PRT
<213> ORGANISM: Artificial Sequence
<220> FEATURE:
<223> OTHER INFORMATION: K09A-L-11 light chain full length
<220> FEATURE:
<221> NAME/KEY: sig_peptide
<222> LOCATION: (1)..(19)

<400> SEQUENCE: 36

Met Ala Pro Val Gln Leu Leu Gly Leu Leu Val Leu Phe Leu Pro Ala
1               5                   10                  15

Met Arg Cys Glu Ile Val Leu Thr Gln Ser Pro Ala Thr Leu Ser Leu
            20                  25                  30

Ser Pro Gly Glu Arg Ala Thr Leu Ser Cys Arg Ala Ser Lys Gly Val
        35                  40                  45

Ser Thr Ser Gly Tyr Ser Tyr Leu His Trp Tyr Gln Gln Lys Pro Gly
    50                  55                  60

Gln Ala Pro Arg Leu Leu Ile Tyr Leu Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

His Ser Arg Asp Leu Pro Leu Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 37
<211> LENGTH: 237
<212> TYPE: PRT
<213> ORGANISM: Artificial Sequence
<220> FEATURE:
<223> OTHER INFORMATION: K09A-L-16 light chain full length
<220> FEATURE:
<221> NAME/KEY: sig_peptide
<222> LOCATION: (1)..(19)

<400> SEQUENCE: 37

Met Ala Pro Val Gln Leu Leu Gly Leu Leu Val Leu Phe Leu Pro Ala
1               5                   10                  15

Met Arg Cys Glu Ile Val Leu Thr Gln Ser Pro Leu Ser Leu Pro Val
            20                  25                  30

Thr Pro Gly Glu Pro Ala Ser Ile Ser Cys Arg Ala Ser Lys Gly Val
        35                  40                  45

Ser Thr Ser Gly Tyr Ser Tyr Leu His Trp Tyr Leu Gln Lys Pro Gly
    50                  55                  60

Gln Ser Pro Gln Leu Leu Ile Tyr Leu Ala Ser Tyr Leu Glu Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Val Gly Val Tyr Tyr Cys Gln
            100                 105                 110

His Ser Arg Asp Leu Pro Leu Thr Phe Gly Gln Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 38
<211> LENGTH: 237
<212> TYPE: PRT
<213> ORGANISM: Artificial Sequence
<220> FEATURE:
<223> OTHER INFORMATION: K09A-L-17 light chain full length
<220> FEATURE:
<221> NAME/KEY: sig_peptide
<222> LOCATION: (1)..(19)

<400> SEQUENCE: 38

Met Ala Pro Val Gln Leu Leu Gly Leu Leu Val Leu Phe Leu Pro Ala
1               5                   10                  15

Met Arg Cys Asp Ile Val Met Thr Gln Thr Pro Leu Ser Leu Pro Val
            20                  25                  30

Thr Pro Gly Glu Pro Ala Ser Ile Ser Cys Arg Ala Ser Lys Gly Val
        35                  40                  45

Ser Thr Ser Gly Tyr Ser Tyr Leu His Trp Tyr Leu Gln Lys Pro Gly
    50                  55                  60

Gln Ser Pro Gln Leu Leu Ile Tyr Leu Ala Ser Tyr Leu Glu Ser Gly

-continued

```
            65                  70                  75                  80
Val Pro Asp Arg Phe Ser Gly Ser Gly Ser Gly Thr Ala Phe Thr Leu
                85                          90                  95

Lys Ile Ser Arg Val Glu Ala Glu Asp Val Gly Leu Tyr Tyr Cys Gln
                100                         105                 110

His Ser Arg Asp Leu Pro Leu Thr Phe Gly Gln Gly Thr Lys Leu Glu
                115                         120                 125

Ile Lys Arg Thr Val Ala Ala Pro Ser Val Phe Ile Phe Pro Pro Ser
        130                         135                 140

Asp Glu Gln Leu Lys Ser Gly Thr Ala Ser Val Val Cys Leu Leu Asn
145                         150                 155                 160

Asn Phe Tyr Pro Arg Glu Ala Lys Val Gln Trp Lys Val Asp Asn Ala
                    165                 170                 175

Leu Gln Ser Gly Asn Ser Gln Glu Ser Val Thr Glu Gln Asp Ser Lys
                180                         185                 190

Asp Ser Thr Tyr Ser Leu Ser Ser Thr Leu Thr Leu Ser Lys Ala Asp
                195                         200                 205

Tyr Glu Lys His Lys Val Tyr Ala Cys Glu Val Thr His Gln Gly Leu
        210                         215                 220

Ser Ser Pro Val Thr Lys Ser Phe Asn Arg Gly Glu Cys
225                     230                     235
```

ANTIBODIES TO HUMAN PROGRAMMED DEATH RECEPTOR PD-1

CROSS-REFERENCE TO RELATED APPLICATIONS

This application is a divisional application of U.S. Ser. No. 14/576,448, filed Dec. 19, 2014, currently pending, which is a divisional application of Ser. No. 13/719,756, filed Dec. 19, 2012, now U.S. Pat. No. 8,952,136, which is a continuation application of U.S. Ser. No. 12/663,950, filed Jun. 21, 2010, now U.S. Pat. No. 8,354,509, which is a § 371 National Stage Application of International Application No. PCT/US2008/007463, international filing date of Jun. 13, 2008, which claims the benefit of U.S. Provisional Application Ser. No. 60/944,583, filed Jun. 18, 2007, now expired.

REFERENCE TO SEQUENCE LISTING SUBMITTED ELECTRONICALLY

The sequence listing of the present application is submitted electronically via EFS-Web as an ASCII formatted sequence listing with a file name "OR06827USDIV3-SEQLIST-01NOV2017.TXT", creation date of Nov. 1, 2017, and a size of 37.6 KB. This sequence listing submitted EFS-Web is part of the specification and is herein incorporated by reference in its entirety.

BACKGROUND OF THE INVENTION

Programmed death receptor 1 (PD-1) is an immunoinhibitory receptor that is primarily expressed on activated T and B cells. Interaction with its ligands has been shown to attenuate T-cell responses both in vitro and in vivo. Blockade of the interaction between PD-1 and one of its ligands, PD-L1, has been shown to enhance tumor-specific CD8$^-$ T-cell immunity and may therefore be helpful in clearance of tumor cells by the immune system.

PD-1 (encoded by the gene Pdcd1) is an Immunoglobulin superfamily member related to CD28, and CTLA-4. PD-1 has been shown to negatively regulate antigen receptor signaling upon engagement of its ligands (PD-L1 and/or PD-L2) The structure of murine PD-1 has been solved as well as the co-crystal structure of mouse PD-1 with human PD-L1 (Zhang, X. et al., *Immunity* 20: 337-347 (2004); Lin et al., *Proc. Natl. Acad. Sci. USA* 105: 3011-6 (2008)). PD-1 and like family members are type I transmembrane glycoproteins containing an Ig Variable-type (V-type) domain responsible for ligand binding and a cytoplasmic tail that is responsible for the binding of signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

Following T cell stimulation, PD-1 recruits the tyrosine phosphatase SHP-2 to the ITSM motif within its cytoplasmic tail, leading to the dephosphorylation of effector molecules such as CD3 zeta, PKC theta and ZAP70 that are involved in the CD3 T cell signaling cascade. The mechanism by which PD-1 downmodulates T cell responses is similar to, but distinct from that of CTLA-4, as both molecules regulate an overlapping set of signaling proteins (Parry et al., *Mol. Cell Biol.* 25: 9543-9553.). Bennett and coworkers have shown that PD-1-mediated inhibition of T-cell signaling is only effective when both activating and inhibitory signals are on the same surface, indicating that the PD-1 signaling mechanism is spatiotemporally determined (Bennett F. et al., *J Immunol.* 170:711-8 (2003)).

PD-1 was shown to be expressed on activated lymphocytes (peripheral CD4$^+$ and CD8$^-$ T cells, B cells and monocytes) and has also been shown to be expressed during thymic development on CD4$^-$CD8$^-$ (double negative) T cells as well as NK-T cells.

The ligands for PD-1 (PD-L1 and PD-L2) are constitutively expressed or can be induced in a variety of cell types, including non-hematopoietic tissues as well as various tumor types. PD-L1 is expressed on B, T, myeloid and dendritic cells (DCs), but also on peripheral cells, like microvascular endothelial cells and non-lymphoid organs like heart, lung etc. In contrast, PD-L2 is only found on macrophages and DCs. The expression pattern of PD-1 ligands is suggestive of a role for PD-1 in maintaining peripheral tolerance and may serve to regulate self-reactive T- and B-cell responses in the periphery. Both ligands are type I transmembrane receptors containing both IgV- and IgC-like domains in the extracellular region. Both ligands contain short cytoplasmic regions with no known signaling motifs.

To date, numerous studies have shown that interaction of PD-1 with its ligands leads to the inhibition of lymphocyte proliferation in vitro and in vivo. Disruption of the PD-1/PD-L1 interaction has been shown to increase T cell proliferation and cytokine production and block progression of the cell cycle. Initial analysis of Pdcd1$^{-/-}$ mice did not identify any drastic immunological phenotype. However aged mice developed spontaneous autoimmune diseases which differ according to the strain onto which the Pdcd1 deficiency was backcrossed. These include lupus-like proliferative arthritis (C57BL/6) (Nishimura H. et al., *Int. Immunol.* 10: 1563-1572 (1998)), fatal cardiomyopathy (BALB/c) (Nishimura H. et al., *Science* 291: 319-322 (2001)) and type I diabetes (NOD) (Wang J. et al., *Proc. Natl. Acad. Sci. U.S.A* 102: 11823-11828 (2005)). Overall, analysis of the knockout animals has led to the understanding that PD-1 functions mainly in inducing and regulating peripheral tolerance. Thus, therapeutic blockade of the PD-1 pathway may be helpful in overcoming immune tolerance. Such selective blockade may be of use in the treatment of cancer or infection as well as in boosting immunity during vaccination (either prophylactic or therapeutic).

The role of PD-1 in cancer is established in the literature. It is known that tumor microenvironment can protect tumor cells from efficient immune destruction. PD-L1 has recently been shown to be expressed on a number of mouse and human tumors (and is inducible by IFN gamma on the majority of PD-L1 negative tumor cell lines) and is postulated to mediate immune evasion (Iwai Y. et al., *Proc. Natl. Acad. Sci. U.S.A.* 99: 12293-12297 (2002); Strome S. E. et al., *Cancer Res.,* 63: 6501-6505 (2003).

In humans, expression of PD-1 (on tumor infiltrating lymphocytes) and/or PD-L1 (on tumor cells) has been found in a number of primary tumor biopsies assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown J. A. et al., *J.*

*Immunol.* 170: 1257-1266 (2003); Dong H. et al., *Nat. Med.* 8: 793-800 (2002); Wintterle et al., *Cancer Res.* 63: 7462-7467 (2003); Strome S. E. et al., *Cancer Res.,* 63: 6501-6505 (2003); Thompson R. H. et al., *Cancer Res.* 66: 3381-5 (2006); Thompson et al., *Clin. Cancer Res.* 13: 1757-61 (2007); Nomi T. et al., *Clin. Cancer Res.* 13:

2151-7. (2007)). More strikingly, PD-ligand expression on tumor cells has been correlated to poor prognosis of cancer patients across multiple tumor types (reviewed in Okazaki and Honjo, *Int. Immunol.* 19: 813-824 (2007)).

Blockade of the PD-1/PD-L1 interaction could lead to enhanced tumor-specific T-cell immunity and therefore be helpful in clearance of tumor cells by the immune system. To address this issue, a number of studies were performed. In a murine model of aggressive pancreatic cancer, T. Nomi et al. (*Clin. Cancer Res.* 13: 2151-2157 (2007)) demonstrated the therapeutic efficacy of PD-1/PD-L1 blockade. Administration of either PD-1 or PD-L1 directed antibody significantly inhibited tumor growth. Antibody blockade effectively promoted tumor reactive CD8$^+$ T cell infiltration into the tumor resulting in the up-regulation of anti-tumor effectors including IFN gamma, granzyme B and perforin. Additionally, the authors showed that PD-1 blockade can be effectively combined with chemotherapy to yield a synergistic effect. In another study, using a model of squamous cell carcinoma in mice, antibody blockade of PD-1 or PD-L1 significantly inhibited tumor growth (Tsushima F. et al., *Oral Oncol.* 42: 268-274 (2006)).

In other studies, transfection of a murine mastocytoma line with PD-L1 led to decreased lysis of the tumor cells when co-cultured with a tumor-specific CTL clone. Lysis was restored when anti-PD-L1 mAb was added (Iwai Y. et al., *Proc. Natl. Acad. Sci. U.S.A.* 99: 12293-12297 (2002)). In vivo, blocking the PD1/PD-L1 interaction was shown to increase the efficacy of adoptive T cell transfer therapy in a mouse tumor model (Strome S. E. et al., *Cancer Res.* 63: 6501-6505 (2003)). Further evidence for the role of PD-1 in cancer treatment comes from experiments performed with PD-1 knockout mice. PD-L1 expressing myeloma cells grew only in wild-type animals (resulting in tumor growth and associated animal death), but not in PD-1 deficient mice (Iwai Y. et al., *Proc. Natl. Acad. Sci. U.S.A.* 99: 12293-12297 (2002)).

In human studies, R. M. Wong et al. (*Int. Immunol.* 19: 1223-1234 (2007)) showed that PD-1 blockade using a fully human anti-PD-1 antibody augmented the absolute numbers of tumor-specific CD8+ T cells (CTLs) in ex vivo stimulation assays using vaccine antigens and cells from vaccinated individuals. In a similar study, antibody blockade of PD-L1 resulted in enhanced cytolytic activity of tumor-associated antigen-specific cytotoxic T cells and increased cytokine production by tumor specific $T_H$ cells (Blank C. et al., *Int. J. Cancer* 119: 317-327 (2006)). The same authors showed that PD-L1 blockade augments tumor-specific T cell responses in vitro when used in combination with anti-CTLA-4 blockade.

Overall, the PD-1/PD-L1 pathway is a well-validated target for the development of antibody therapeutics for cancer treatment. Anti-PD-1 antibodies may also be useful in chronic viral infection. Memory CD8$^+$ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. (Barber et al., *Nature* 439: 682-687 (2006)) showed that mice infected with a laboratory strain of LCMV developed chronic infection resulting in high levels of virus in the blood and other tissues. These mice initially developed a robust T cell response, but eventually succumbed to the infection upon T cell exhaustion. The authors found that the decline in number and function of the effector T cells in chronically infected mice could be reversed by injecting an antibody that blocked the interaction between PD-1 and PD-L1.

Recently, it has been shown that PD-1 is highly expressed on T cells from HIV infected individuals and that receptor expression correlates with impaired T cell function and disease progression (Day et al., *Nature* 443:350-4 (2006).; Trautmann L. et al., *Nat. Med.* 12: 1198-202 (2006)). In both studies, blockade of the ligand PD-L1 significantly increased the expansion of HIV-specific, IFN-gamma producing cells in vitro.

Other studies also implicate the importance of the PD-1 pathway in controlling viral infection. PD-1 knockout mice exhibit better control of adenovirus infection than wild-type mice (Iwai et al., *J. Exp. Med.* 198:39-50 (2003)). Also, adoptive transfer of HBV-specific T cells into HBV transgenic animals initiated hepatitis (Isogawa M. et al., *Immunity* 23:53-63 (2005)). The disease state of these animals oscillates as a consequence of antigen recognition in the liver and PD-1 upregulation by liver cells.

BRIEF SUMMARY OF THE INVENTION

The invention provides isolated antibodies and antibody fragments that bind to human and cyno PD-1. In some embodiments, the antibody or antibody fragment blocks binding of human PD-L1 and human PD-L2 to human PD-1. In some embodiments, the PD-1 antibody or antibody fragment of the invention includes one or more CDRs (antibody Complementarity—Determining Regions) selected from SEQ ID NOs: 9, 10, 11, 12, 13, 14, 15, 16, 17, 18, 19 and 20; and in further embodiments, includes one or more heavy chain CDRs of SEQ ID NOs:12, 13, 14, 18, 19 and 20 and/or the light chain CDRs of SEQ ID NOs: 9, 10, 11, 15, 16 and 17. In some embodiments, the antibody or antibody fragment is a chimeric antibody, human antibody, humanized antibody or a fragment thereof.

In one embodiment, the invention provides an isolated antibody or antibody fragment which binds to human PD-1 comprising: a light chain comprising CDRs SEQ ID NOs: 9, 10 and 11, or variants of any said sequences; and/or a heavy chain comprising CDRs SEQ ID NOs: 12, 13 and 14, or variants of any said sequences.

In another embodiment, the invention provides an isolated antibody or antibody fragment which binds to human PD-1 comprising: a light chain comprising CDRs SEQ ID NOs: 15, 16 and 17 or variants of any said sequences; and/or a heavy chain comprising CDRs SEQ ID NOs: 18, 19 and 20, or variants of any said sequences.

In one embodiment, the invention comprises an antibody or antigen binding fragment comprising a heavy chain variable region SEQ ID NO: 5 or a variant thereof; and/or a light chain variable region comprising SEQ ID NO: 6 or a variant thereof.

In one embodiment, the invention comprises an antibody or antigen binding fragment comprising a heavy chain variable region SEQ ID NO: 7 or a variant thereof and/or a light chain variable region comprising SEQ ID NO: 8 or a variant thereof.

In one embodiment, the invention comprises an antibody or antigen binding fragment comprising a heavy chain variable region comprising amino acid residues 20 to 139 of SEQ ID NO: 30 or a variant thereof; and/or a light chain variable region comprising amino acid residues 20 to 130 of SEQ ID NO: 32 or a variant thereof.

In one embodiment, the invention comprises an antibody or antigen binding fragment comprising a heavy chain variable region comprising amino acid residues 20 to 139 of SEQ ID NO: 30 or a variant thereof; and/or a light chain variable region comprising amino acid residues 20 to 130 of SEQ ID NO: 33 or a variant thereof.

In one embodiment, the invention comprises an antibody or antigen binding fragment comprising a heavy chain variable region comprising amino acid residues 20 to 139 of SEQ ID NO: 30 or a variant thereof; and/or a light chain variable region comprising amino acid residues 20 to 130 of SEQ ID NO: 34 or a variant thereof.

In one embodiment, the invention comprises an antibody or antigen binding fragment comprising a heavy chain variable region comprising an amino acid sequence having at least 90% homology to amino acid residues 20 to 139 of SEQ ID NO: 30; and/or a light chain variable region comprising and an amino acid sequence having at least 90% homology to amino acid residues 20 to 130 of SEQ ID NO: 32, 33 or 34.

In one embodiment, the invention provides an isolated antibody or antibody fragment which binds to human PD-1 comprising: a heavy chain comprising amino acid residues 20 to 466 of SEQ ID NO: 31 or a variant thereof, and/or a light chain comprising amino acid residues 20 to 237 of SEQ ID NO: 36 or a variant thereof.

In one embodiment, the invention provides an isolated antibody or antibody fragment which binds to human PD-1 comprising: a heavy chain comprising the amino acid residues 20 to 466 of SEQ ID NO: 31 or a variant thereof, and/or a light chain comprising the amino acid residues 20 to 237 of SEQ ID NO: 37 or a variant thereof.

In one embodiment, the invention provides an isolated antibody or antibody fragment which binds to human PD-1 comprising: a heavy chain comprising amino acid residues 20 to 466 of SEQ ID NO: 31 or a variant thereof, and/or a light chain comprising amino acid residues 20 to 237 of SEQ ID NO: 38 or a variant thereof.

In one embodiment, the invention provides an isolated antibody or antibody fragment which binds to human PD-1 comprising: a heavy chain comprising amino acid residues 20 to 469 of SEQ ID NO: 35 or a variant thereof, and/or a light chain comprising amino acid residues 20 to 237 of SEQ ID NO: 36 or a variant thereof.

In one embodiment, the invention provides an isolated antibody or antibody fragment which binds to human PD-1 comprising: a heavy chain comprising amino acid residues 20 to 469 of SEQ ID NO: 35 or a variant thereof, and/or a light chain comprising amino acid residues 20 to 237 of SEQ ID NO: 37 or a variant thereof.

In one embodiment, the invention provides an isolated antibody or antibody fragment which binds to human PD-1 comprising: a heavy chain comprising amino acid residues 20 to 469 of SEQ ID NO: 35 or a variant thereof, and/or a light chain comprising amino acid residues 20 to 237 of SEQ ID NO: 38 or a variant thereof.

In any of the above embodiments, the variant of the antibody or antibody fragment of the invention may comprise one, two or three conservatively modified amino acid substitutions.

In any of the above embodiments, the antibody or antibody fragment of the invention may comprise a human heavy chain constant region or a variant thereof, wherein the variant comprises up to 20 conservatively modified amino acid substitutions; and/or a human light chain constant region or a variant thereof, wherein the variant comprises up to 20 conservatively modified amino acid substitutions. In some embodiments, the variant may comprise up to 10 conservatively modified amino acid substitutions. In some embodiments, the variant may comprise up to 5 conservatively modified amino acid substitutions. In some embodiments, the variant may comprise up to 3 conservatively modified amino acid substitutions. In any of the above embodiments, the human heavy chain constant region or variant thereof may be of the IgG1 or IgG4 isotype.

In any of the above described embodiments, the antibody or antibody fragment of the invention may bind human PD-1 with a $K_D$ of about 100 pM or lower. In another embodiment, the antibody or antibody fragment may bind human PD-1 with a $K_D$ of about 30 pM or lower. In another embodiment, the antibody or antibody fragment may bind human PD-1 with about the same $K_D$ as an antibody having a heavy chain comprising the amino acid sequence of SEQ ID NO: 31 and a light chain comprising the amino acid sequence of SEQ ID NO: 32. In another embodiment, the antibody or antibody fragment may bind human PD-1 with about the same $K_D$ as an antibody having a heavy chain comprising the amino acid sequence of SEQ ID NO: 31 and a light chain comprising the amino acid sequence of SEQ ID NO: 33.

In any of the above described embodiments, the antibody or antibody fragment of the invention may bind human PD-1 with a $k_{assoc}$ of about $7.5 \times 10^5$ l/M·s or faster. In one embodiment, the antibody or antibody fragment may bind human PD-1 with a $k_{assoc}$ of about $1 \times 10^6$ l/M·s or faster.

In any of the above described embodiments, the antibody or antibody fragment may bind human PD-1 with a $k_{dissoc}$ of about $2 \times 10^{-5}$ l/s or slower. In one embodiment, the antibody or antibody fragment may bind human PD-1 with a $k_{dissoc}$ of about $2.7 \times 10^{-5}$ l/s or slower. In one embodiment, the antibody or antibody fragment may bind human PD-1 with a $k_{dissoc}$ of about $3 \times 10^{-5}$ l/s or slower.

$K_D$, $k_{assoc}$ and $k_{dissoc}$ values can be measured using any available method. In preferred embodiments, the dissociation constant is measured using bio-light interferometry (for example, the ForteBio Octet method described in Example 2). In other preferred embodiments, the disassociation constant can be measured using surface plasmon resonance (e.g. Biacore) or Kinexa.

Further, in any of the above described embodiments, the antibody or antibody fragment of the invention may block binding of human PD-L1 or human PD-L2 to human PD-1 with an $IC_{50}$ of about 1 nM or lower. The blockade of ligand binding can be measured and the $IC_{50}$ calculated using any method known in the art, for example, the FACS or FMAT methods described in the Examples herein.

The invention also comprises an antibody or antibody fragment which competes for a binding epitope on human PD-1 with any of the antibodies described above, and which blocks the binding of human PD-L1 or human PD-L2 to human PD-1 with an $IC_{50}$ of about 1 nM or lower.

The invention also comprises an antibody or antibody fragment which competes for a binding epitope on human PD-1 with any of the antibodies described above, and which binds human PD-1 with a $K_D$ of about 100 pM or lower. In one embodiment, the antibody or antibody fragment binds human PD-1 with a $K_D$ of about 30 pM or lower.

The invention also comprises an antibody or antibody fragment which competes for a binding epitope on human PD-1 with any of the antibodies described above, and which binds human PD-1 with about the same $K_D$ as an antibody having a heavy chain comprising the amino acid sequence of SEQ ID NO: 31 and a light chain comprising the amino acid sequence of SEQ ID NO: 32.

The invention also comprises an antibody or antibody fragment that competes for a binding epitope on human PD-1 with any of the antibodies described above, and which binds human PD-1 with about the same $K_D$ as an antibody having a heavy chain comprising the amino acid sequence of SEQ ID NO: 31 and a light chain comprising the amino acid sequence of SEQ ID NO: 33.

The invention also comprises an antibody or antibody fragment which competes for a binding epitope on human PD-1 with any of the antibodies described above, and which binds human PD-1 with a $k_{assoc}$ of about $7.5\times10^5$ 1/M·s or faster. In one embodiment, the antibody or antibody fragment may bind human PD-1 with a $k_{assoc}$ of about $1\times10^6$ 1/M·s or faster.

The invention also comprises an antibody or antibody fragment which competes for a binding epitope on human PD-1 with any of the antibodies described above, and which binds human PD-1 with a $k_{dissoc}$ of about $2\times10^{-5}$ 1/s or slower. In one embodiment, the antibody or antibody fragment may bind human PD-1 with a $k_{dissoc}$ of about $2.7\times10^{-5}$ 1/s or slower. In one embodiment, the antibody or antibody fragment may bind human PD-1 with a $k_{dissoc}$ of about $3\times10^{-5}$ 1/s or slower.

In some embodiments, the antibody or antibody fragments of the invention are chimeric antibodies or fragments of chimeric antibodies.

In some embodiments, the antibody or antibody fragments of the invention are human antibodies or fragments of human antibodies.

In some embodiments, the antibody or antibody fragments of the invention are humanized antibodies or fragments of humanized antibodies.

In some embodiments, the antibody fragments of the invention are Fab, Fab', Fab'-SH, Fv, scFv, or F(ab')2 antibody fragments.

In some embodiments, the antibody fragments of the invention are diabodies.

The invention also comprises bispecific antibodies comprising any one of the antibody or antibody fragments described above that bind to human PD-1.

In some embodiments, the isolated anti-PD-1 antibodies and antibody fragments of the invention increase T cell activation as measured by typical means known to one skilled in the art (including, without limitation, increased immune cell proliferation, increased cytokine secretion or expression of activation markers such as CD25 and/or CD69).

In any of the above described embodiments, the antibody or antibody fragment of the invention may enhance the immune response after stimulation with Staphylococcus Enterotoxin B or Tetanus Toxoid ex vivo or in vivo. The increased immune activation may be determined using methods known to anyone skilled in the art, for example, quantifying proliferation of immune cells (such as T cells) or cytokine production by immune cells (for example production of IFNγ or IL-2 by T cells).

The invention also comprises nucleic acids encoding the anti-PD-1 antibodies and antibody fragments of the invention. Included in the invention are nucleic acids encoding any one of the amino acid sequences disclosed in SEQ ID NOS: 5 to 20 and 30-38 (with or without the leader sequences). Also included within the invention are nucleic acids comprising SEQ ID NOS:1 to 4 and 21 to 29 (with or without the nucleic acids encoding the leader sequences).

The invention also comprises cells and expression vectors comprising nucleic acids encoding the antibodies or antibody fragments of the invention. Further, the invention comprises a method of producing an antibody or antibody fragment of the invention comprising: (a) culturing the host cell comprising a nucleic acid encoding an antibody or antibody fragment of the invention in culture medium under conditions wherein the nucleic acid sequence is expressed, thereby producing polypeptides comprising the light and heavy chain variable regions; and (b) recovering the polypeptides from the host cell or culture medium.

The invention also comprises compositions comprising an antibody or antibody fragment of the invention in combination with a pharmaceutically acceptable carrier or diluent.

The invention also comprises a method of increasing the activity of an immune cell, comprising administering to a subject in need thereof a therapeutically effective amount of an antibody or antibody fragment of the invention. In one embodiment, the method may be used to treat cancer. In another embodiment, the method may be use to treat an infection or infectious disease. In yet another embodiment, the method may be used as a vaccine adjuvant. In some embodiments, the method comprises further administering a second therapeutic agent or treatment modality.

In some embodiments, the invention comprises a method of increasing the activity of an immune cell, comprising administering to a subject in need thereof a therapeutically effective amount of an antibody or antibody fragment of the invention, and further comprising measuring T cell activation ex vivo in a sample derived from the subject, wherein an increase in T cell activity indicates that the treatment should be continued. In other embodiments, the invention comprises a method of increasing the activity of an immune cell, comprising administering to a subject in need thereof a therapeutically effective amount of an antibody or antibody fragment of the invention, and further comprising measuring T cell activation ex vivo in a sample derived from the subject, wherein an increase in T cell activity predicts the likelihood that the treatment will be successful. In one embodiment, the increase in T cell activity is determined by: (i) measuring SEB induced production of one or more cytokines selected from the group consisting of: IL-2, TNFα, IL-17, IFNγ, GM-CSF, RANTES, IL-6, IL-8, IL-5 and IL-13; or (ii) measuring TT induced production of a cytokine selected from the group consisting of: IL-2, TNFα, IL-17, IFNγ, GM-CSF, RANTES, IL-6, IL-8, IL-5 and IL-13.

The invention also comprises the use of an anti-PD-1 antibody or antibody fragment of the invention for the preparation of a medicament to increase immune response.

The invention also comprises the use of an anti-PD-1 antibody or antibody fragment of the invention for the preparation of a medicament to treat cancer.

The invention also comprises the use of an anti-PD-1 antibody or antibody fragment of the invention as a vaccine adjuvant.

The invention also comprises an immunoconjugate comprising an anti-PD-1 antibody or antibody fragment of the invention, linked to a therapeutic agent such as a bacterial toxin or a radiotoxin. Non-limiting examples of cytotoxic agents include taxol, cytochalasin B, mitomycin, etoposide and vincristine or other antimetabolites, alkylating agents, antibiotics and antimitotics.

The invention also comprises a method of increasing the activity, or reducing the downmodulation, of an immune cell comprising contacting the immune cell with any one of the antibodies or antibody fragments of the invention. This method could be used to treat cancer or infectious diseases (such as chronic viral infections), or could be used as an adjuvant to a prophylactic or therapeutic vaccine.

The invention also comprises a method of increasing an immune response to an antigen, comprising contacting an immune cell with an antigen and an anti-PD-1 antibody or an antibody fragment such that an immune response to the antigen is increased or enhanced. This method could be conducted in vivo (in a subject) or ex vivo.

In some embodiments, an anti-PD-1 antibody or antibody fragment may be combined with a second therapeutic agent or treatment modality. In one embodiment, an anti-PD-1 antibody or antibody fragment may be combined with cancer treatments involving the application of recombinant cytokines or secreted immune factors. Non-limiting examples of combinations include combining anti-PD-1 antibody with recombinant IL-2 or recombinant IFNα2 for the treatment of melanoma or renal cell carcinoma. Recombinant IL-2 enhances T cell outgrowth in cancer patients. Recombinant IFNα2 inhibits cancer cell growth but also increases expression of the inhibitory ligands for PD-1 on cancer cells, antigen-presenting cells and other somatic cells in the treated patients. Anti-PD-1 can be combined with other cytokines that might be considered useful for the treatment of cancer or infectious diseases.

In some embodiments, anti-PD-1 antibodies or antibody fragments can be combined with a vaccine to prevent or treat cancer or infectious disease. As a non-limiting example, anti-PD-1 could be combined with a protein, peptide or DNA vaccine containing one or more antigens which are relevant to the cancer or infection to be treated, or a vaccine comprising of dendritic cells pulsed with such a) antigen. Another embodiment includes the use of anti-PD-1 with (attenuated) cancer cell or whole virus vaccines. One embodiment involves a combination of anti-PD-1 therapy with a whole cell cancer vaccine that is engineered to secrete GM-CSF.

In some embodiments, anti-PD-1 antibodies or antibody fragments can be combined with treatment that is considered to be standard of care in cancer or infectious disease. Rationale for such combinations is that concurrent increased immune activation by anti-PD-1 will induce or facilitate initial clinical response to standard of care treatment, induce durable clinical response and long-term immune control of disease.

In one embodiment, treatment with anti-PD-1 antibodies or antibody fragments may be combined with chemotherapy. Chemotherapy using cytotoxic agents will result in cancer cell death thereby increasing release of tumor antigens. Such increased availability of tumor antigen may result in synergy with anti-PD-1 treatment. A non-limiting example is provided by the use of decarbazine or temozolomide for the treatment of melanoma and gemcitabine for pancreatic cancer.

In one embodiment, treatment with anti-PD-1 antibodies or antibody fragments may be combined with radiotherapy. Radiotherapy induces cancer cell death and increasing availability of tumor antigens for presentation and activation of immune cells.

In another embodiment, treatment with anti-PD-1 antibodies or antibody fragments may be combined with surgery to remove cancer cells from a subject.

In other embodiments, anti-PD-1 antibodies or antibody fragments may be combined with therapies which may result in synergy with PD-1 blockade including targeted agents used for hormone deprivation or inhibition of angiogenesis, or targeting proteins active in tumor cells, all resulting in enhanced tumor cell death and availability of immune stimulating tumor antigens. In combination with an anti-PD-1 antibody or antibody fragment, increased T cell activation may result in durable immune control of cancer.

In some embodiments, an anti-PD-1 antibody or antibody fragment may be combined with another therapeutic antibody useful for the treatment of cancer or infectious disease. A non-limiting example is provided by the combination of anti-PD-1 with an antibody targeting Her2/neu or targeting the EGF receptor. In another non-limiting example, an anti-PD-1 antibody or antibody fragment is combined with treatment targeting VEGF or its receptors. In another embodiment, an anti-PD-1 antibody or antibody fragment is combined with anti-CTLA-4. In yet another nonlimiting example, anti-PD-1 is combined with an antibody that targets RSV.

BRIEF DESCRIPTION OF THE DRAWINGS

FIGS. 1A and 1B show the results of experiments demonstrating that antibodies immobilized from hybridoma supernatants are able to reduce IL-2 secretion by Jurkat E6.2.11 cells stimulated with immobilized anti-CD3 and soluble anti-CD28.

FIG. 2A is a graph showing dose dependent binding of anti-PD-1 antibodies to purified PD-1/Fc in a protein ELISA. FIG. 2B is a graph showing dose dependent binding of anti PD-1 antibodies to PD-1 expressed on the surface of CHO cells transfected with hPD-1 in a CELISA.

FIG. 3A is a graph showing dose dependent inhibition of binding of PD-L1 by hPD-1.08A and hPD-1.09A and to a lesser extent by J116. FIG. 3B is a graph showing dose dependent inhibition of PD-L2.

FIG. 5 shows concentration dependent IFNγ secretion.

DETAILED DESCRIPTION OF THE INVENTION

Abbreviations and Definitions

Figure 2B:
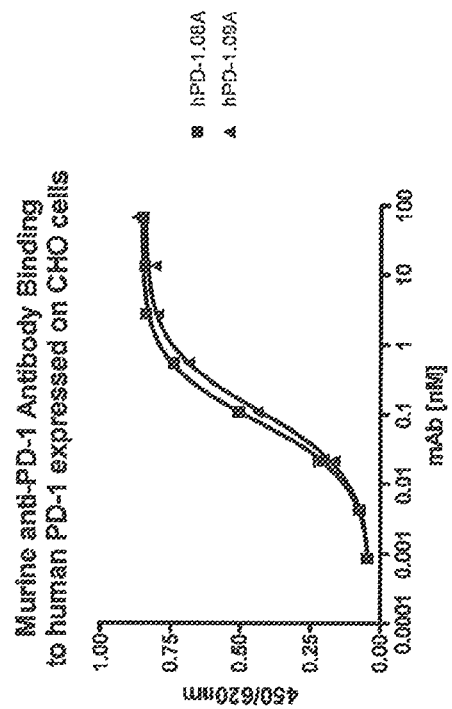
FIGS. 2A and 2B show the results of experiments demonstrating that antibodies against human PD-1 bind to PD-1.

Throughout the detailed description and examples of the invention the following abbreviations will be used:
hPD-1.08A Murine monoclonal anti-hPD-1 antibody
hPD-1.09A Murine monoclonal anti-hPD-1 antibody
08A-VH VH isolated from hPD-1.08A hybridoma
08A-VK VK isolated from hPD-1.08A hybridoma
09A-VH VH isolated from hPD-1.09A hybridoma
09A-VK VK isolated from hPD-1.09A hybridoma
c109A Chimeric IgG1 version of hPD1.09A antibody
c109A-VH Chimeric heavy chain, consisting of murine 09A-VH fused to hIgG1 constant region
c109A-VK Chimeric light chain, consisting of murine 09A-VK fused to human kappa constant region
109A-H Humanized IgG1 09A heavy chain sequence with zero back mutations.
409A-H Humanized IgG4-09A heavy chain sequence with zero FWR back mutations
K09A-L-11 Humanized 09A-kappa sequence with framework originally having CDR1 length of 11 AAs
K09A-L-16 Humanized 09A-kappa sequence with framework originally having CDR1 length of 16 AAs
K09A-L-17 Humanized 09A-kappa sequence with framework originally having CDR1 length of 17 AAs
h409A11 Humanized IgG4 version of 09A antibody comprising a heavy chain comprising the sequence of 409A-H and a light chain comprising the sequence of K09A-L-11
h409A16 Humanized IgG4 version of 09A antibody comprising a heavy chain comprising the sequence of 409A-H and a light chain comprising the sequence of K09A-L-16
h409A17 Humanized IgG4 version of 09A antibody comprising a heavy chain comprising the sequence of 409A-H and a light chain comprising the sequence of K09A-L-17
hPD-1 human PD-1 protein
CDR Complementarity determining region in the immunoglobulin variable regions, defined using the Kabat numbering system
EC50 concentration resulting in 50% efficacy or binding
ELISA Enzyme-linked immunosorbant assay
FW Antibody framework region: the immunoglobulin variable regions excluding the CDR regions
HRP Horseradish peroxidase
IL-2 interleukin 2
IFN interferon
IC50 concentration resulting in 50% inhibition
IgG Immunoglobulin G
Kabat An immunoglobulin alignment and numbering system pioneered by Elvin A Kabat
mAb Monoclonal antibody
MES 2-(N-morpholino)ethanesulfonic acid
NHS Normal human serum
PCR Polymerase chain reaction
SAM sheep anti-mouse (IgG) polyclonal antibody
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region "Antibody" refers to any form of antibody that exhibits the desired biological activity, such as inhibiting binding of a ligand to its receptor, or by inhibiting ligand-induced signaling of a receptor. Thus, "antibody" is used in the broadest sense and specifically covers, but is not limited to, monoclonal antibodies (including full length monoclonal antibodies), polyclonal antibodies, and multispecific antibodies (e.g., bispecific antibodies).

"Antibody fragment" and "antibody binding fragment" mean antigen-binding fragments and analogues of an antibody, typically including at least a portion of the antigen binding or variable regions (e.g. one or more CDRs) of the parental antibody. An antibody fragment retains at least some of the binding specificity of the parental antibody. Typically, an antibody fragment retains at least 10% of the parental binding activity when that activity is expressed on a molar basis. Preferably, an antibody fragment retains at least 20%, 50%, 70%, 80%, 90%, 95% or 100% or more of the parental antibody's binding affinity for the target. Examples of antibody fragments include, but are not limited to, Fab, Fab', F(ab')$_2$, and Fv fragments; diabodies; linear antibodies; single-chain antibody molecules, e.g., sc-Fv, unibodies (technology from Genmab); nanobodies (technology from Domantis); domain antibodies (technology from Ablynx); and multispecific antibodies formed from antibody fragments. Engineered antibody variants are reviewed in Holliger and Hudson (2005) Nat. Biotechnol. 23:1126-1136.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the CH3 domains.

A "Fab' fragment" contains one light chain and a portion of one heavy chain that contains the $V_H$ domain and the $C_H1$ domain and also the region between the $C_H1$ and $C_H^2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

A "single-chain Fv antibody" (or "scFv antibody") refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448.

A "domain antibody fragment" is an immunologically functional immunoglobulin fragment containing only the variable region of a heavy chain or the variable region of a light chain. In some instances, two or more $V_H$ regions are covalently joined with a peptide linker to create a bivalent domain antibody fragment. The two $V_H$ regions of a bivalent domain antibody fragment may target the same or different antigens.

An antibody fragment of the invention may comprise a sufficient portion of the constant region to permit dimerization (or multimerization) of heavy chains that have reduced disulfide linkage capability, for example where at least one of the hinge cysteines normally involved in inter-heavy chain disulfide linkage is altered as described herein. In another embodiment, an antibody fragment, for example one that comprises the Fc region, retains at least one of the biological functions normally associated with the Fc region when present in an intact antibody, such as FcRn binding, antibody half life modulation, ADCC function, and/or complement binding (for example, where the antibody has a glycosylation profile necessary for ADCC function or complement binding).

The term "chimeric" antibody refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, Proc. Natl. Acad. Sci. USA 81:6851-6855).

"Humanized" forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Cur. Op. Struct. Biol. 2:593-596 (1992).

The term "hypervariable region," as used herein, refers to the amino acid residues of an antibody which are responsible for antigen-binding. The hypervariable region comprises amino acid residues from a "complementarity determining region" or "CDR," defined by sequence alignment, for example residues 24-34 (L1), 50-56 (L2) and 89-97 (L3) in the light chain variable domain and 31-35 (H1), 50-65 (H2) and 95-102 (H3) in the heavy chain variable domain; see Kabat et al., 1991, Sequences of proteins of Immunological Interest, 5th Ed. Public Health Service, National Institutes of Health, Bethesda, Md. and/or those residues from a "hypervariable loop" (HVL), as defined structurally, for example, residues 26-32 (L1), 50-52 (L2) and 91-96 (L3) in the light chain variable domain and 26-32 (H1), 53-55 (H2) and 96-101 (H3) in the heavy chain variable domain; see Chothia and Leskl, 1987, J. Mol. Biol. 196:901-917. "Framework" or "FR" residues are those variable domain residues other than the hypervariable region residues as herein defined.

A "human antibody" is an antibody that possesses an amino acid sequence corresponding to that of an antibody produced by a human and/or has been made using any of the techniques for making human antibodies disclosed herein. This definition specifically excludes a humanized antibody that comprises non-human antigen-binding residues.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, for example, U.S. Pat. No. 4,816,567). The "monoclonal antibodies" may also be isolated from phage antibody libraries using the techniques described in Clackson et al., 1991, *Nature* 352:624-628 and Marks et al., 1991, *J. Mol. Biol.* 222:581-597, for example. The monoclonal antibodies herein specifically include "chimeric" antibodies.

As used herein, the term "immune cell" includes cells that are of hematopoietic origin and that play a role in the immune response. Immune cells include lymphocytes, such as B cells and T cells; natural killer cells; myeloid cells, such as monocytes, macrophages, eosinophils, mast cells, basophils, and granulocytes.

As used herein, an "immunoconjugate" refers to an anti-PD-1 antibody, or a fragment thereof, conjugated to a therapeutic moiety, such as a bacterial toxin, a cytotoxic drug or a radiotoxin. Toxic moieties can be conjugated to antibodies of the invention using methods available in the art.

The following nucleic acid ambiguity codes are used herein: R=A or G; Y=C or T; M=A or C; K=G or T; S=G or C; and W=A or T.

As used herein, a sequence "variant" refers to a sequence that differs from the disclosed sequence at one or more amino acid residues but which retains the biological activity of the resulting molecule.

"Conservatively modified variants" or "conservative amino acid substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth below as follows:

| Exemplary Conservative Amino Acid Substitutions | |
|---|---|
| Original residue | Conservative substitution |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

As used herein, "% identity" between two sequences refers to a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. For example, the percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "about" refers to a value that is within an acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" or "comprising essentially of can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

"Specifically" binds, when referring to a ligand/receptor, antibody/antigen, or other binding pair, indicates a binding reaction which is determinative of the presence of the protein, e.g., PD-1, in a heterogeneous population of proteins and/or other biologics. Thus, under designated conditions, a specified ligand/antigen binds to a particular receptor/antibody and does not bind in a significant amount to other proteins present in the sample.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell.

"Effective amount" encompasses an amount sufficient to ameliorate or prevent a symptom or sign of the medical condition. Effective amount also means an amount sufficient to allow or facilitate diagnosis. An effective amount for a particular subject may vary depending on factors such as the condition being treated, the overall health of the patient, the method route and dose of administration and the severity of side affects. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

Monoclonal Antibodies

Monoclonal antibodies to PD-1 can be made according to knowledge and skill in the art of injecting test subjects with PD-1 antigen and then isolating hybridomas expressing antibodies having the desired sequence or functional characteristics.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., 1990, *Nature*, 348:552-554. Clackson et al., 1991, *Nature*, 352:624-628, and Marks et al., 1991, *J. Mol. Biol.* 222:581-597 describe the isolation of murine and human antibodies, respectively, using phage libraries. Subsequent publications describe the production of high affinity (nM range) human antibodies by chain shuffling (Marks et al., 1992, *Bio/Technology*, 10:779-783), as well as combinatorial infection and in vivo recombination as a strategy for constructing very large phage libraries (Waterhouse et al., 1993, *Nuc. Acids. Res.* 21:2265-2266). Thus, these techniques are viable alternatives to traditional monoclonal antibody hybridoma techniques for isolation of monoclonal antibodies.

Chimeric Antibodies

The antibody DNA also may be modified, for example, by substituting the coding sequence for human heavy- and light-chain constant domains in place of the homologous murine sequences (U.S. Pat. No. 4,816,567; Morrison, et al., 1984, *Proc. Natl Acad. Sci. USA*, 81:6851), or by covalently joining to the immunoglobulin coding sequence all or part of the coding sequence for non-immunoglobulin material (e.g., protein domains). Typically such non-immunoglobulin material is substituted for the constant domains of an antibody, or is substituted for the variable domains of one antigen-combining site of an antibody to create a chimeric bivalent antibody comprising one antigen-combining site having specificity for an antigen and another antigen-combining site having specificity for a different antigen.

Humanized and Human Antibodies

A humanized antibody has one or more amino acid residues from a source that is non-human. The non-human amino acid residues are often referred to as "import" residues, and are typically taken from an "import" variable domain. Humanization can be performed generally following the method of Winter and co-workers (Jones et al., 1986, *Nature* 321:522-525; Riechmann et al., 1988, *Nature*, 332: 323-327; Verhoeyen et al., 1988, *Science* 239:1534-1536), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., 1987, *J. Immunol.* 151:2296; Chothia et al., 1987, *J. Mol. Biol.* 196:901). Another method uses a particular framework derived from the consensus sequence of all human antibodies of a particular subgroup of light or heavy chains. The same framework may be used for several different humanized antibodies (Carter et al., 1992, *Proc. Natl. Acad. Sci. USA* 89:4285; Presta et al., 1993, *J. Immnol.* 151:2623).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Humanization of antibodies is a straightforward protein engineering task. Nearly all murine antibodies can be humanized by CDR grafting, resulting in the retention of antigen binding. See, Lo, Benny, K. C., editor, in *Antibody Engineering: Methods and Protocols*, volume 248, Humana Press, New Jersey, 2004.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 1993, *Proc. Natl. Acad. Sci. USA* 90:2551; Jakobovits et al., 1993, *Nature* 362:255-258; Bruggermann et al., 1993, *Year in Immunology* 7:33; and Duchosal et al., 1992, *Nature* 355:258. Human antibodies can also be derived from phage-display libraries (Hoogenboom et al., 1991, *J. Mol. Biol.* 227:381; Marks et al., *J. Mol. Biol.* 1991, 222:581-597; Vaughan et al., 1996, *Nature Biotech* 14:309).

Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., 1992, *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the antibody. Protein A can be used to purify antibodies that are based on human .gamma.1, .gamma.2, or .gamma.4 heavy chains (Lindmark et al., 1983, *J. Immunol. Meth.* 62:1-13). Protein G is recommended for all mouse isotypes and for human .gamma.3 (Guss et al., 1986, *EMBO J* 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In one embodiment, the glycoprotein may be purified using adsorption onto a lectin substrate (e.g. a lectin affinity column) to remove fucose-containing glycoprotein from the preparation and thereby enrich for fucose-free glycoprotein.

Pharmaceutical Formulations

The invention comprises pharmaceutical formulations of a PD-1 antibody or antibody fragment of the invention. To prepare pharmaceutical or sterile compositions, the antibody or fragment thereof is admixed with a pharmaceutically acceptable carrier or excipient, see, e.g., *Remington's Pharmaceutical Sciences and U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, N.Y.; Lieberman, et al. (eds.) (1990) *Pharmaceutical Dosage Forms: Tablets*, Marcel Dekker, N.Y.; Lieberman, et al. (eds.) (1990) *Pharmaceutical Dosage Forms: Disperse Systems*, Marcel Dekker, N.Y.; Weiner and Kotkoskie (2000) *Excipient Toxicity and Safety*, Marcel Dekker, Inc., New York, N.Y.).

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration and oral administration. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. In one embodiment, the binding compound of the invention is administered intravenously. In another embodiment, the binding compound of the invention is administered subcutaneously.

Alternately, one may administer the antibody in a local rather than systemic manner, for example, via injection of the antibody directly into the site of action, often in a depot or sustained release formulation. Furthermore, one may administer the antibody in a targeted drug delivery system.

Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Antibodies, antibody fragments, and cytokines can be provided by continuous infusion, or by doses at intervals of, e.g., one day, one week, or 1-7 times per week. Doses may be provided intravenously, subcutaneously, intraperitoneally, cutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with disease and/or a reduction in the severity of such symptoms that will or are expected to develop with said disease. The terms further include ameliorating existing symptoms, preventing additional symptoms, and ameliorating or preventing the underlying causes of such symptoms. Thus, the terms denote that a beneficial result has been conferred on a vertebrate subject with a disease.

As used herein, the term "therapeutically effective amount" or "effective amount" refers to an amount of an anti-PD-1 antibody or fragment thereof, that when administered alone or in combination with an additional therapeutic agent to a cell, tissue, or subject is effective to prevent or ameliorate the disease or condition to be treated. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent are well known in the art, see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa.

The pharmaceutical composition of the invention may also contain other agent, including but not limited to a cytotoxic, cytostatic, anti-angiogenic or antimetabolite agent, a tumor targeted agent, an immune stimulating or immune modulating agent or an antibody conjugated to a cytotoxic, cytostatic, or otherwise toxic agent. The pharmaceutical composition can also be employed with other therapeutic modalities such as surgery, chemotherapy and radiation.

Typical veterinary, experimental, or research subjects include monkeys, dogs, cats, rats, mice, rabbits, guinea pigs, horses, and humans.

Therapeutic Uses for the Antibody and Antibody Fragments of the Invention

The antibody or antigen binding fragments of the invention, which specifically bind to human PD-1, can be used to increase, enhance, stimulate or up-regulate an immune response. The antibodies and antibody fragments of the invention are particularly suitable for treating subjects having a disorder that can be treated by increasing the T-cell mediated immune response. Preferred subjects include human patients in need of enhancement of an immune response.

Cancer

The antibody or antigen binding fragments of the invention can be used to treat cancer (i.e., to inhibit the growth or survival of tumor cells). Preferred cancers whose growth may be inhibited using the antibodies of the invention include cancers typically responsive to immunotherapy, but also cancers that have not hitherto been associated with immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the invention includes refractory or recurrent malignancies whose growth may be inhibited using the antibodies of the invention.

The antibody or antibody fragments of the invention can be used alone or in combination with: other anti-neoplastic agents or immunogenic agents (for example, attenuated cancerous cells, tumor antigens (including recombinant proteins, peptides, and carbohydrate molecules), antigen presenting cells such as dendritic cells pulsed with tumor derived antigen or nucleic acids, immune stimulating cytokines (for example, IL-2, IFNa2, GM-CSF), and cells transfected with genes encoding immune stimulating cytokines such as but not limited to GM-CSF); standard cancer treatments (for example, chemotherapy, radiotherapy or surgery); or other antibodies (including but not limited to antibodies to VEGF, EGFR, Her2/neu, VEGF receptors, other growth factor receptors, CD20, CD40, CTLA-4, OX-40, 4-IBB, and ICOS).

Infectious Diseases

The antibody or antibody fragments of the invention can also be used to prevent or treat infections and infectious disease. The antibody or antibody fragments can be used alone, or in combination with vaccines, to stimulate the immune response to pathogens, toxins, and self-antigens. The antibodies or antigen-binding fragment thereof can be used to stimulate immune response to viruses infectious to humans, such as, but not limited to, human immunodeficiency viruses, hepatitis viruses class A, B and C, Epstein Barr virus, human cytomegalovirus, human papilloma viruses, herpes viruses. The antibodies or antigen-binding fragment thereof can be used to stimulate immune response to infection with bacterial or fungal parasites, and other pathogens.

Vaccination Adjuvant

The antibody or antibody fragments of the invention can be used in conjunction with other recombinant proteins and/or peptides (such as tumor antigens or cancer cells) in order to increase an immune response to these proteins (i.e., in a vaccination protocol).

For example, anti-PD-1 antibodies and antibody fragments thereof may be used to stimulate antigen-specific immune responses by coadministration of an anti-PD-1 antibody with an antigen of interest (e.g., a vaccine). Accordingly, in another aspect the invention provides a method of enhancing an immune response to an antigen in a subject, comprising administering to the subject: (i) the antigen; and (ii) an anti-PD-1 antibody of the invention or antigen-binding portion thereof, such that an immune response to the antigen in the subject is enhanced. The antigen can be, for example, a tumor antigen, a viral antigen, a bacterial antigen or an antigen from a pathogen. Non-limiting examples of such antigens include, without limitation, tumor antigens, or antigens from the viruses, bacteria or other pathogens.

Th2 Mediated Diseases

Anti-PD-1 antibodies and antibody fragments of the invention can also be used to treat Th2 mediated diseases, such as asthma and allergy. This is based on the finding that the antibodies of the invention can help induce a Th1 response. Thus, the antibodies of the invention can be used to in Th2 mediated diseases to generate a more balanced immune response.

Ex-Vivo Activation of T Cells

The antibodies and antigen fragments of the invention can also be used for the ex vivo activation and expansion of antigen specific T cells and adoptive transfer of these cells into recipients in order to increase antigen-specific T cells against tumor. These methods may also be used to activate T cell responses to infectious agents such as CMV. Ex vivo activation in the presence of anti-PD-1 antibodies may be expected to increase the frequency and activity of the adoptively transferred T cells.

Other Combination Therapies

As previously described, anti-PD-1 antibodies of the invention can be coadministered with one or other more therapeutic agents, e.g., a cytotoxic agent, a radiotoxic agent or an immunosuppressive agent. The antibody can be linked to the agent (as an immunocomplex) or can be administered separately from the agent. In the latter case (separate administration), the antibody can be administered before, after or concurrently with the agent or can be co-administered with other known therapies.

Antibodies and antigen binding fragments of the invention can also be used to increase the effectiveness of donor engrafted tumor specific T cells.

Non-Therapeutic Uses for the Antibody and Antibody Fragments of the Invention

A market for anti-PD-1 antibodies for non-therapeutic uses already exists, as demonstrated by the commercial sales of J116, and J105 monoclonal anti-hPD-1 antibodies sold by eBioscience of San Diego, Calif., USA, for use in flow cytometric analysis, immunohistochemistry and in vitro functional assays; and mab1086, a monoclonal anti-hPD-1 antibody sold by R&D Systems of Minneapolis, Minn., USA, for use in flow cytometry, Western blots and ELISA. Antibodies of the invention may be used for any non-therapeutic purpose now served by J116, J105 and/or Mab1086.

The antibody of the invention may be used as an affinity purification agent.

The antibody may also be useful in diagnostic assays, e.g., for detecting expression of PD-1 in specific cells, tissues, or serum. For diagnostic applications, the antibody typically will be labeled (either directly or indirectly) with a detectable moiety. Numerous labels are available which can be generally grouped into the following categories: biotin, fluorochromes, radionucleotides, enzymes, iodine, and biosynthetic labels.

The antibody of the present invention may be employed in any known assay method, such as competitive binding assays, direct and indirect sandwich assays, and immunoprecipitation assays. Zola, *Monoclonal Antibodies. A Manual of Techniques*, pp. 147-158 (CRC Press, Inc. 1987).

The antibody may also be used for in vivo diagnostic assays. Generally, the antibody is labeled with a radionuclide (such as $^{111}$In, $^{99}$Tc, $^{4}$C, $^{3}$1I, $^{125}$I, $^{3}$H, $^{32}$P $^{35}$S or $^{18}$F) so that the antigen or cells expressing it can be localized using immunoscintiography or positron emission tomography.

Deposit of Materials

DNA constructs encoding the variable regions of the heavy and light chains of the humanized antibodies h409A11, h409A16 and h409A17 have been deposited with the American Type Culture Collection Patent Depository (10801 University Blvd., Manassas, Va.). The plasmid containing the DNA encoding the heavy chain of h409A-11, h409A-16 and h409A-17 was deposited on Jun. 9, 2008 and identified as 081469_SPD-H. The plasmid containing the DNA encoding the light chain of h409A11 was deposited on Jun. 9, 2008 and identified as 0801470_SPD-L-11. The plasmid containing the DNA encoding the light chain of h409A16 was deposited on Jun. 9, 2008 and identified as 0801471_SPD-L-16. The plasmid containing the DNA encoding the light chain of h409A17 was deposited on Jun. 9, 2008 and was designated 0801472_SPD-L-17. The deposits were made under the provisions of the Budapest Treaty on the International Recognition of the Deposit of Microorganisms for the Purpose of Patent Procedure and the Regulations thereunder (Budapest Treaty).

The foregoing written specification is considered to be sufficient to enable one skilled in the art to practice the invention. The present invention is not to be limited in scope by the culture deposited, since the deposited embodiment is intended as a single illustration of one aspect of the invention and any culture that is functionally equivalent is within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

The invention will be more fully understood by reference to the following examples. They should not, however, be construed as limiting the scope of this invention. All literature and patent citations mentioned herein are expressly incorporated by reference.

EXAMPLES

Example 1: Immunization and Selection of Anti PD-1 Antibodies

Immunization of Mice with hPD-1 cDNA

To generate antibodies against the human PD-1 (hPD-1') receptor, a cDNA encoding the open reading frame of the hPD-1 receptor was obtained by PCR and subcloned into vector pcDNA3.1 (Invitrogen, Carlsbad, Calif.). Next, CHO-K1 cells were stably transfected with hPD-1, and expression was monitored using flow cytometry. CHO-K1 clones were isolated expressing human PD-1 on their membranes and named CHO-hPD1.

Mice were immunized by gene gun immunization using a Helios gene gun (BioRad) and DNA coated gold bullets (BioRad) following manufacturers instructions. Briefly, 1 µm gold particles were coated with hPD-1 cDNA (cloned into pcDNA3.1) and, where indicated, commercial expression vectors for mouse Flt3L and mouse GM-CSF in a 2:1:1 ratio (both from Aldevron, Fargo N.D.). A total of 1 µg of plasmid DNA was used to coat 500 µg of gold bullets.

Specifically, 7-8 week-old female BALB/C mice were immunized on the ear by gene gun receiving 2, 3, or 4 cycles of a shot on both ears (see Table I). One mouse received a final booster with $5\times10^6$ CHO-hPD1 cells in the peritoneal cavity. Approximately, a 1:1000 anti-hPD-1 titers was detectable in mouse serum after two DNA immunizations by cell ELISA using CHO-hPD-1 versus CHO-K1 parental cells. Four days after the final immunization, mice were sacrificed, and erythrocyte-depleted spleen cell populations were prepared as described previously (Steenbakkers et al., 1992, *J. Immunol. Meth.* 152:69-77; Steenbakkers et al., 1994, *Mol. Biol. Rep.* 19:125-134) and frozen at −140° C.

Selected B-cells were cultured and immortalized as described in Steenbakkers et al., 1994, *Mol. Biol. Rep.* 19:125-134. Briefly, selected B cells were mixed with 7.5% (v/v) T-cell supernatant and 50,000 irradiated (2,500 RAD) EL-4 B5 nursing cells in a final volume of 200 µL DMEM/HAM's F12/10% Bovine Calf Serum, in 96-well flat-bottomed tissue culture plates. On day eight, supernatants were screened for their anti-hPD-1 reactivity by CHO-hPD-1 cell ELISA using the following procedure. CHO-K1 and CHO-hPD1 cells were cultured to confluency in flatbottom 96-well plates in 50 µL DMEM/HAM'S F12, 10% FBS. Next, 50 µL of immunoglobulin-containing supernatant was added for 1 hr at 37° C. After three washes with PBS-Tween, 100 µL (1:1000 diluted) goat-anti-mouse—horseradish peroxidase (HRP, Southern, Birmingham, Ala., USA) in DMEM/HAM'S F12/10% FBS was added for 1 hour at 37° C. After three washes with PBS-Tween, immobilized immunoglobulins were visualized with UPO/TMB (Biomerieux, Boxtel, Netherlands).

From this B-cell culture, 13 hPD-1 reactive supernatants were identified and shown to inhibit Jurkat T cell activation when immobilized on plastic, and B-cell clones from positive wells were immortalized by mini-electrofusion following published procedures (Steenbakkers et al., 1992, *J. Immunol. Meth.* 152:69-77; Steenbakkers et al., 1994, *Mol. Biol. Rep.* 19:125-134). Specifically, B-cells were mixed with $10^6$ NS-1 myeloma cells, and serum was removed by washing with DMEM/HAM's F12. Next, cells were treated with pronase solution for three minutes and subsequently washed with fusion medium. Electrofusion was performed in a 50 µL fusion chamber by an alternating electric field of 30 s, 2 MHz, 400 V/cm followed by a square, high field pulse of 10 µs, 3 kV/cm and again an alternating electric field of 30 s, 2 MHz, 400 V/cm. Finally, the content of the

TABLE I

Immunization schedule used to induce hPD-1 specific antibody titers in Balb/c mice.

|  | Week 1 | Week 4 | Week 7 | Week 8 | Week 9 | Week 10 | Week 11 |
|---|---|---|---|---|---|---|---|
| Mouse 730 | 2 shots hPD1 pCDNA3.1 | 2 shots hPD1 pCDNA3.1 |  | 2 shots hPD1 pCDNA3.1 | Harvest of spleen cells |  |  |
| Mouse 731 | 2 shots hPD1 pCDNA3.1 | 4 shots hPD1 pCDNA3.1 |  |  | 5 million CHO-hPD1 | Harvest of spleen cells |  |
| Mouse738 | 2 shots hPD1 pCDNA3.1 (mFlt3L + mGM-CSF) | 2 shots hPD1 pCDNA3.1 (mFlt3L + mGM-CSF) | 2 shots hPD1 pCDNA3.1 (mFlt3L + mGM-CSF) |  |  | 2 shots hPD1 pCDNA3.1 (mFlt3L + mGM-CSF) | Harvest of spleen cells |

Selection of Anti-PD-1 Antibody Producing B Cells

To select B cell clones producing anti-human-PD-1 antibodies, $2\times10^7$ erythrocyte-depleted spleen cells from hPD-1 DNA immunized mice, i.e., mouse 730, 731 and 738 (see Table I), were pooled for a B-cell culture. Spleen cells were incubated in DMEM/HAM's F12/10% Calf Serum (Hyclone, Logan, Utah, USA) for one hour at 37° C. in a plastic culture flask to remove monocytes. Non-adherent cells were submitted to one round of negative panning on CHO-K1 cells, followed by positive panning on CHO-hPD1 cells. Both selection procedures were performed for one hour at 37° C. on confluently grown cultures in 21 cm² petridishes or T25 culture flasks (cell cultures were irradiated before use, to a total dose of 2000 RAD). After the positive panning, unbound cells were removed by washing ten times with PBS supplemented with 0.132% $CaCl_2.2H_2O$ and 0.1% $MgCl_2.6H_2O$. Finally, bound B-cells were harvested by trypsin treatment.

fusion chamber was transferred to hybridoma selection medium and plated into a 96-well plate under limiting dilution conditions. On day 14 after fusion, the cultures were examined for hybridoma growth and screened for the presence of antibody reactivity to hPD-1. This procedure yielded five different anti-hPD-1 hybridomas, named hPD-1.05A, hPD-1.06B, hPD-1.08A, hPD-1.09A and hPD-1.13A, that were subcloned by limiting dilution to safeguard their integrity and further cultured to produce antibody. Supernatants obtained from these hybridomas strongly inhibited the IL-2 production from Jurkat E6.2.11 cells upon anti-CD3/anti-CD28 stimulation (see FIG. 1 and text below).

Jurkat E6.1 cells (American Type Culture Collection) were subcloned by limiting dilution using standard methodology and subclones were tested for enhanced capacity to produce IL-2 upon cross-linking of CD3 and CD28. A high IL-2 producing subclone was obtained and subsequently named Jurkat E6.2.11 and used in further assays. Costar 3370 96-well assay plates were coated overnight at 4° C. with 5 μg/mL Sheep Anti-Mouse Ig (SAM). Excess of SAM was removed and plates were blocked for 1 hr at room temperature with 200 μL/well PBS/10% Fetal Bovine Serum. After three washes with PBS, wells were coated with 100 μL/well anti-CD3 (OKT3; 10 or 60 ng/mL) for 1 hr at 37° C. After three washes with PBS, 50 μL/well PBS/10% Fetal Bovine Serum and 50 μL/well B-cell- or hybridoma supernatant was added for 30 min at 37° C. After three washes with PBS, 120 μL/well of cell suspension, Jurkat E6.2.11 cells ($2 \times 10^5$ cells/well+0.5 μg/mL anti-CD28 (Sanquin #M1650, Central Laboratory for Bloodtransfusion, Amsterdam, NL) in DMEM/F12/10% Fetal Bovine Serum) was added. After a 6 h culture, supernatant was examined for IL-2 production using a standard sandwich ELISA with anti-hIL-2 capture and biotinylated detection antibody pairs from Pharmingen and Streptavidin-Horse Radish Peroxidase (Southern Biotech) as a detection reagent. To determine the potency of these antibodies as compared with PD-L1, a small group of mAbs was produced on a larger scale. The mAbs were purified using Protein G affinity chromatography (see Example 2). Purified antibodies, hPD-L1/Fc (recombinant human B7-H1/Fc chimera, R&D systems) or mouse IgG1 kappa (from Sigma) as a negative control were coated at identical concentrations on plates with anti-CD3 as described above. Jurkat E6.2.11 cells and anti-CD28 were added for six hours, and T-cell activation was measured by IL-2 produced in the supernatant. Two of the antibodies (hPD1.08A and hPD1.09A) showed an 8-10 fold more potent inhibition compared to immobilized PD-L1/Fc.

Example 2: Purification and Characterization of Murine Anti-PD-1 Antibodies

Stabilization of Anti-PD-1 Producing Hybridomas and Purification of Anti-PD-1 Antibodies Clonal cell populations were obtained for each of the hybridomas by subjecting them to multiple rounds (>4) of limiting dilution. Stable hybridoma cells were then cultured under serum-free conditions using CELLine bioreactors (Integra-biosciences) for six to eight days. Cells were seeded in the inner chamber in serum-free media at a density of $3 \times 10^6$ c/mL in 15 mL and expanded to approximately $4 \times 10^7$ c/mL over eight days. The outer chamber was filled with media supplemented with up to 10% BCS (bovine calf serum). On day six to eight, the inner chamber culture was harvested, washed with 15 mL SF media and re-innoculated with hybridoma cells. Bioreactor supernatant and wash were combined and clarified by centrifugation. The resulting supernatant was filtered through a 0.22 μM filter membrane. For antibody purification, supernatants were diluted 1:1 in high salt binding buffer (1M Glycine/2M NaCl, pH 9.0), and mAbs were purified using Protein G HiTrap 5 mL column (GE healthcare). After washing with PBS, bound antibodies were eluted using 0.1 M Glycine pH=2.7, followed by pH neutralization using 3 M Tris. Finally, the buffer was exchanged for PBS using PD-10 gel-filtration columns (GE healthcare), and antibodies were concentrated using Ultra-15 centrifugal concentrators (Amicon) and quantified using spectrophotometry.

Commercial Antibodies

The following commercial antibodies were used in various studies described herein: Anti-PD-1 antibody clone J116 (#14-9989) was purchased from eBioscience. Anti-CTLA-4 clone 14D3 (mAb 16-1529) was purchased from eBioscience. Anti-PD-1 clone 192106 (mAb1086) was purchased from R&D systems (#mAb1086). Isotype control antibody mIgG1, kappa, clone MOPC21 was purchased from Sigma (#M9269). Isotype controls mIgG1 kappa (mAb 16-4714) and IgG2a kappa (mAb 16-4724) were purchased from eBioscience.

Binding Analysis

Protein-based and cell-based ELISA ('CELISA') experiments were used to determine apparent binding affinities (reported as EC50 values). In some cases, the binding of the anti-PD-1 antibodies was compared to that of commercial anti-PD-1 antibodies J116 (eBiosciences) and Mab1086 (R&D systems).

Figure 2A:
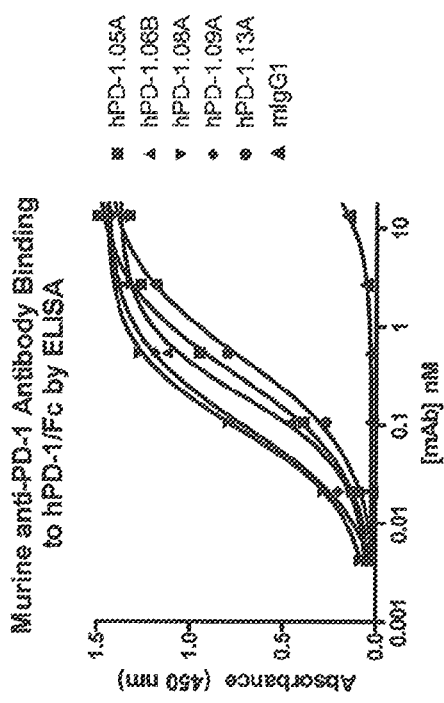

A protein ELISA was used for determination of the relative binding of antibodies to human PD-1/Fc. hPD-1/Fc (R & D Systems) was immobilized onto Maxisorp 96-well plates (Nunc) by incubation for 4 h at room temperature (or overnight at 4° C.). Nonspecific binding sites were blocked by incubation with 3% BSA in PBST for one hour at room temperature. After coating, the plates were washed three times with PBST. Dilutions of anti-PD-1 antibodies were prepared in binding buffer (PBS containing 0.1% Tween 20 and 0.3% BSA) and incubated with the immobilized fusion protein for one hour at 25° C. After binding, the plates were washed three times with PBST, incubated for one hour at 25° C. with peroxidase-labeled goat anti-mouse IgG (Southern Biotech) diluted 1/4,000 in binding buffer, washed again, and developed using TMB. ELISA results are shown in FIG. 2. The concentration of half-maximal binding is reported as a measure of relative binding affinity (Table II).

Binding to CHO-hPD-1 cells was also assessed by CELISA. For CELISA, CHO-hPD-1 cells were cultured to 80 to 100 percent confluency in 50 μL culture medium (DMEM/HAM'S F12, 10% FBS). Next, 50 μL media containing various concentrations of purified mAb were added for one hour at 37° C. After three washes with PBS-Tween, 100 μL goat-anti-mouse-HRP (Southern Biotech cat #1030-05) (diluted 1:1000 in culture medium) was added for one hour at 37° C. After three additional washes with PBS-Tween, immobilized immunoglobulins were visualized with colorimetric peroxidase substrate TMB (BD Biosciences). Absorbance increase due to peroxidase activity (450 nm) was measured in a microtiter plate reader. FIG. 2 shows the dose-response relation between concentration and binding for antibodies hPD-1.08A and hPD-1.09A. The results of the protein and cell binding studies are summarized in Table II.

Kinetic Analysis by Bio-Light Interferometry (ForteBio)

To further characterize the binding characteristics of the antibodies, each was profiled using bio-light interferometry on the Octet system (ForteBio, Menlo Park, Calif.) to elucidate binding kinetics and calculate equilibrium binding constants. This assay was performed by coupling PD-1-Fc fusion protein (R&D Systems) to amine-reactive biosensors (Fortebio) using standard amine chemistry. Anti-PD-1 mAb binding to and dissociation from the biosensors was then observed at various antibody concentrations. Specifically, amine-reactive biosensors were pre-wet by immersing them in wells containing 0.1M MES pH=5.5 for 5 minutes. The biosensors were then activated using a 0.1M NHS/0.4M EDC mixture for 5 minutes. PD-1/Fc fusion protein (R & D systems) was coupled by immersing the biosensors in a solution of 12 ug/mL PD-1/Fc in 0.1M MES for 7.5 minutes. The biosensor surface was quenched using a solution of 1M ethanolamine for 5 minutes. Biosensors were equilibrated in PBS for 5 minutes. Association of anti-PD-1 mAbs was observed by placing the biosensors in wells containing various antibody concentrations (10-80 nM purified antibody >99% by SDS-PAGE in PBS) and monitoring interferometry for 30 minutes. Dissociation was measured after transfer of the biosensors into PBS and monitoring of the interferometry signal for 60 minutes. The observed on and off rates ($k_{obs}$ and $k_d$) were fit using a 1:1 binding global fit model comprising all concentrations tested, and the equilibrium binding constant $K_D$ was calculated. Results from the kinetic studies are presented in Table II, and FIG. 6 below.

varying concentrations of anti-PD-1 antibody and a constant concentration (600 ng/mL) of hPD-L1/Fc or hPD-L2/Fc fusion protein (both from R&D Systems), labeled with a fluorescent dye (AlexaFluor 647, Invitrogen) in a 96-well plate. The mixture was equilibrated for 90 minutes at 37° C. and read using an AB8200 Cellular Detection Analyzer

TABLE II

Biochemical characterization summary of murine anti-PD-1 mAbs.

| | Binding Analysis | | Ligand Blockade | | | Kinetic Analysis | | |
|---|---|---|---|---|---|---|---|---|
| | ELISA | CELISA | FACS | FMAT | | Fortebio Octet | | |
| | EC50 (pM) | EC50 (pM) | IC50 (pM) | IC50 (pM) | | $k_{assoc}$ | $k_{dissoc}$ | $K_D$ |
| mAb | hPD-1/Fc | hPD-1/CHO | PD-L1 | PD-L1 | PD-L2 | 1/s | 1/Ms | M |
| 05A | 338 | | 15 | | | 1.62E+05 | 1.11E−04 | 6.90E−10 |
| 06B | 135 | | 160 | | | 8.32E+04 | 9.74E−05 | 1.17E−09 |
| 08A | 76 | 79 | 0.9 | 0.73 | 2.1 | 1.25E+06 | 3.03E−05 | 2.41E−11 |
| 09A | 123 | 113 | 0.8 | 0.90 | 1.7 | 1.64E+06 | 3.60E−05 | 2.20E−11 |
| 13A | 485 | | 64 | | | 1.46E+05 | 4.16E−04 | 2.85E−09 |
| J116 | 410 | 349 | 106 | >100 | 44 | 8.24E+04 | 1.50E−04 | 1.82E−09 |
| mAb086 | 59 | >10000 | >10000 | >10000 | >10000 | 2.45E+05 | 1.68E−04 | 6.86E−10 |

Two of the monoclonal antibodies, hPD-1.08A and hPD-1.09A, bound considerably more tightly than any other mAb tested using this assay, with $K_D$ determined to be 24 and 22 pM for hPD-1.08A and hPD-1.09A, respectively. Compared to the other anti-PD-1 antibodies tested, the increased affinity is due to a slower off-rate and a significantly faster on—rate measured for hPD-1.08A and hPD-1.09A.

Ligand Blockade

Blockade of ligand binding studied using flow cytometry. CHO cells expressing human PD-1 were dissociated from adherent culture flasks and mixed with varying concentrations of anti-PD-1 antibody and a constant concentration (600 ng/mL) of unlabeled hPD-L1/Fc or recombinant human PD-L2/Fc fusion protein (both from R&D Systems) in a 96-well plate. The mixture was equilibrated for 30 minutes on ice, washed three times with FACS buffer (PBS containing 1% BCS and 0.1% sodium azide), and incubated with FITC labeled goat anti-human Fc for a further 15 minutes on ice. The cells were washed again with FACS buffer and analyzed by flow cytometry. Data were analyzed with Prism (GraphPad Software, San Diego, Calif.) using non-linear regression, and IC50 values were calculated.

Calculated $IC_{50}$ data are summarized in Table II. Antibodies 05A, 06B and 13A were determined to demonstrate a $K_D$ between 600 pM and 3 nM for the binding of hPD-1. Despite the tight binding, these antibodies each demonstrated $IC_{50}$>10 nM for the blockade of hPD-L1 binding to hPD-1. The commercially available anti-PD-1 antibody J116 (eBiosciences) weakly competed with PD-L1 for binding, having a calculated IC50 outside the range of this experiment (>100, nM). Control mouse IgG1 does not compete with PD-L1 for PD-1 binding. In contrast, the high affinity antibodies hPD-1.08A and hPD-1.09A inhibited PD-L1 binding with $IC_{50}$ values below 1 nM, whereas PD-L2 binding was blocked with $IC_{50}$ values around 1-2 nM (Table II). PD-L2 was reported earlier to bind to PD-1 with a two- to six-fold higher affinity than does PD-L1 (Youngnak P. et al., 2003, *Biochem. Biophys. Res. Commun.* 307, 672-677).

Figures 3A, 3B:
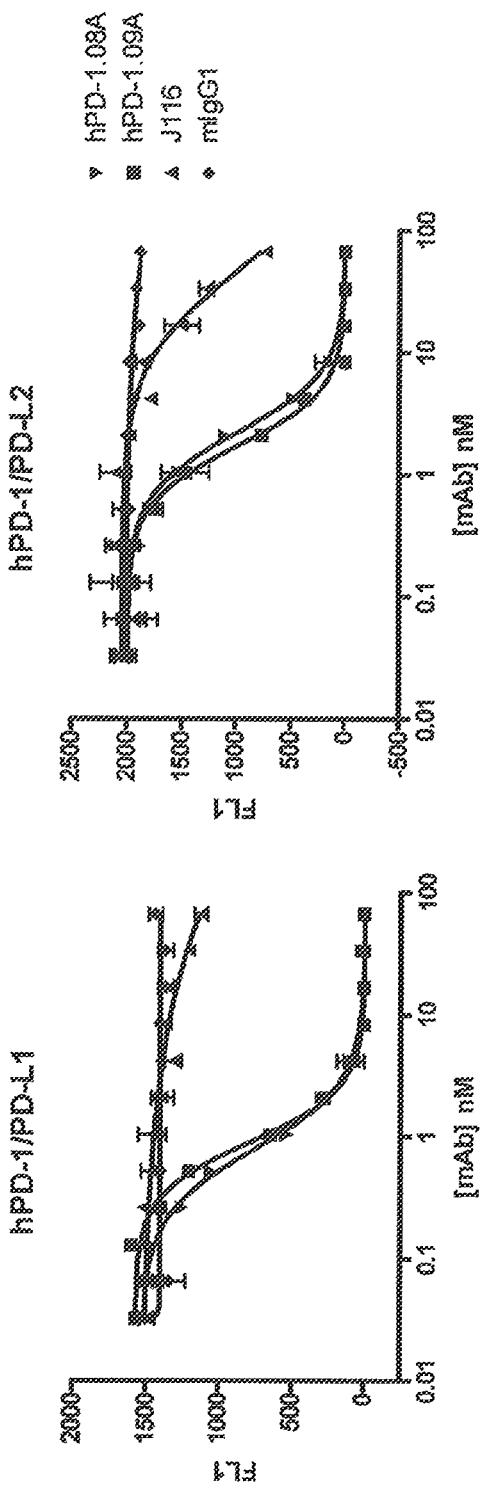
FIGS. 3A and 3B show results of FMAT experiments demonstrating that the antibodies against PD-1 compete for binding of PD-L1 and PD-L2 to CHO cells transfected with human PD-1.

Ligand blockade was confirmed using a homogeneous competition assay and detection using fluorometric microvolume assay technology (FMAT). Briefly, CHO.hPD-1 were dissociated from adherent culture flasks, mixed with (Applied Biosystems, Foster City, Calif.). Data was analyzed with Prism (GraphPad Software, San Diego, Calif.) using non-linear regression, and IC50 values were calculated. FIG. 3 shows results of a dose-response experiment indicating that the magnitude of ligand blockade is determined by antibody concentration. Binding of both hPD-L1/Fc and hPD-L2/Fc to CHO-hPD-1 cells can be completely inhibited by hPD-1.08A, hPD-1.09A and (to a lesser extent) by J116 in a dose-dependent fashion. Calculated $IC_{50}$ data are summarized in Table II. Confirming the results obtained using flow cytometry, the high affinity antibodies hPD-1.08A and hPD-1.09A inhibited PD-L1 binding with $IC_{50}$ values below 1 nM.

Species Cross-Reactivity

To assess the species cross-reactivity of the antibodies, the mouse and cynomolgus macaque PD-1 receptors were cloned by PCR and stably transfected CHO-K1 cells were generated. The antibodies were tested for binding to the cynomolgus receptor using a CELISA. Commercial antibody J116, hPD-1.08A and hPD-1.09A were found to bind with equal affinity to human and cynomolgus PD-1 and block binding of hPD-L1/Fc and hPD-L2/Fc to cynomolgus PD-1 with similar efficacy as compared to human PD-1. This is not surprising because the amino acid sequence of the extracellular portion of cynomolgus PD-1 was found to be 97% identical to that of human PD-1. In addition to PD-1 from cynomolgus macaques, hPD-1.08A and hPD-1.09A also functionally blocked PD-1 from rhesus macaques in SEB stimulated blood cell cultures described in Example 3. None of the antibodies tested bound mouse PD-1 with detectable affinity in any of the assays used.

In summary, five anti-PD-1 monoclonal antibodies were purified and characterized, which were isolated based on their ability to modulate Jurkat function. These antibodies bound tightly to PD-1 (with dissociation constants in the 20 pM to 3 nM range) and were capable of blocking the interaction with both PD-L1 and PD-L2 with varying IC50 values. Four of these anti-hPD-1 mAbs were considerably better than the best available commercial anti-PD-1 mAbs. Each of the antibodies, when added in solution acted as receptor antagonists, ultimately enhancing T cell responses (see Example 3).

Example 3: Functional Profiling of Anti-PD-1 Antibodies

Human T Cell Response to SEB is Enhanced by hPD-1.08A and hPD-1.09A

Anti-PD-1 antibodies were tested for their capacity to enhance T cell activity in vitro using blood cells from healthy volunteers. One assay used to characterize the functional consequence of blocking human PD-1 receptor utilized Staphylococcus enterotoxin B (SEB) to engage and activate all T cells expressing the Vβ3 and Vβ8 T cell receptor chain.

Figure 4:
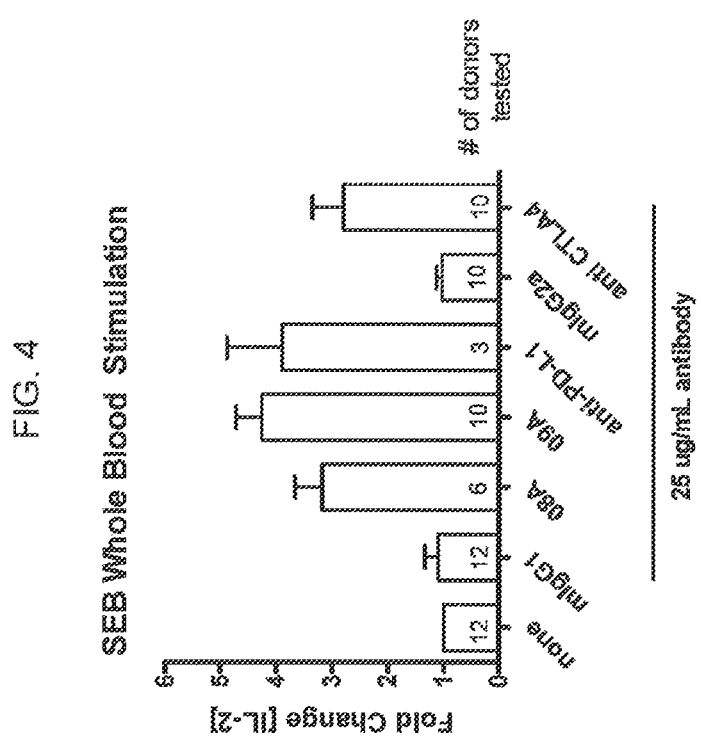
FIG. 4 is a bar graph which shows results of experiments demonstrating that SEB-stimulated IL-2 production by healthy donor blood cells is enhanced in the presence of anti-PD-1, anti PD-L1 or anti-CTLA-4 antibodies. Bars show the average fold increase in IL-2 across donors (±SEM). Numbers inside each bar indicate the number of donors represented. Mouse (m)IgG1 is the isotype control for anti-PD-1.08A (08A), anti-PD-1.09A (09A) and anti-PD-L1. Mouse (m) IgG2a is the isotype control for anti-CTLA-4. Each IL-2 value is compared to its own control to determine the fold change (fold change IL-2 of 4 means 400% increase in IL-2 production when compared to SEB alone). None=SEB alone.

Healthy human donor blood was obtained and diluted 1:10 into culture medium. Diluted whole blood was plated (150 µl per well) in 96-well round-bottom plates and pre-incubated for 30-60 min with mAb and varying concentrations. SEB was then added at various concentrations ranging from 10 ng/mL to 10 µg/mL. Supernatants were collected after 2 to 4 days of culture and the amount of IL-2 produced was quantified using ELISA (described in Example 1) or using standard multiplex technology (Luminex platform—Biosource cytokine detection kits). Titration of SEB from 100 ng/mL up to 10 µg/mL significantly stimulated IL-2 production by whole-blood cells. Usually, depending on the donor, 100 to 1000 pg/mL IL-2 was detectable by ELISA 2-4 days after stimulation with 1 µg/mL of SEB. Addition of hPD-1.08A and hPD-1.09A enhanced IL-2 production over control mouse IgG1, on average 2 to 4 fold at the highest antibody concentration tested (25 µg/mL). The stimulation index was averaged for experiments performed with a set of independent healthy volunteers (FIG. 4). These experiments demonstrated that both hPD-1.08A and hPD-1.09A enhanced IL-2 production upon SEB stimulation of diluted whole-blood cells. Both PD-1 and PD-L1 (but not PD-L2) expression levels were upregulated (quantified by flow cytometry) over time after SEB stimulation of whole blood cells. Anti-PD-L1 monoclonal antibody (clone MIH5, Ebiosciences #16-5982) and anti-CTLA-4 (clone 14D3, eBiosciences #16-1529) also induced an increase in IL-2 production under similar conditions, a finding that further validated the use of the SEB stimulation assay to quantify T cell activity after manipulation of costimulatory pathways (FIG. 4). The enhanced IL-2 production by anti-PD-1 antibodies was found to be dose-dependent. In addition to IL-2, by Luminex technology levels of TNFα, IL-17, IL-7, IL-6 and IFNγ were also found to be significantly modulated by hPD-1.08A and hPD-1.09A. The results of these experiments indicate that hPD-1.08A and hPD-1.09 can be used to stimulate human T cell responses.

Anti-PD-1 antibody, hPD-1.09A, was further tested for its capacity to enhance T cell activity in vitro using blood cells derived from cancer patients. Blood from patients with advanced melanoma (1 patient) or prostate cancer (3 patients) was tested following the above protocol. Results of the cytokine quantitation are presented in Table III as fold increase of cytokine produced when cells are stimulated in the presence of 25 ug/mL hPD-1.09A compared to SEB stimulation in the absence of antibody. In summary, hPD-1.09A was found to increase the SEB induced IL-2 production 2 to 3.5 fold for each of the 4 patients. Similarly production of TNFα, IL-17 and IFNγ was enhanced, and production of IL-5 and IL-13 was decreased. These experiments indicate that hPD-1.09A has the ability to stimulate T cell responses in cancer patients. Further, these experiments suggest a preference towards Th1 responses.

TABLE III

SEB-stimulated cytokine production in the presence of hPD-1.09A

| patient | cancer type | Fold change in cytokine level ||||||| 
|---|---|---|---|---|---|---|---|---|
| | | IL-2 | TNFα | IFNγ | IL-5 | IL-6 | IL-13 | IL-17 |
| A | prostate | 3.4 | 2.0 | 1.9 | 0.7 | 2.1 | 0.8 | 1.8 |
| B | prostate | 2.1 | 1.5 | 1.2 | 0.4 | 2.2 | 0.6 | 2.6 |
| C | prostate | 2.0 | 2.4 | 2 | 0.9 | 2.4 | 1.1 | 2.4 |
| D | melanoma | 2.0 | 1.9 | 1.5 | 0.4 | 1.9 | 0.5 | 2.0 |

Figure 5:
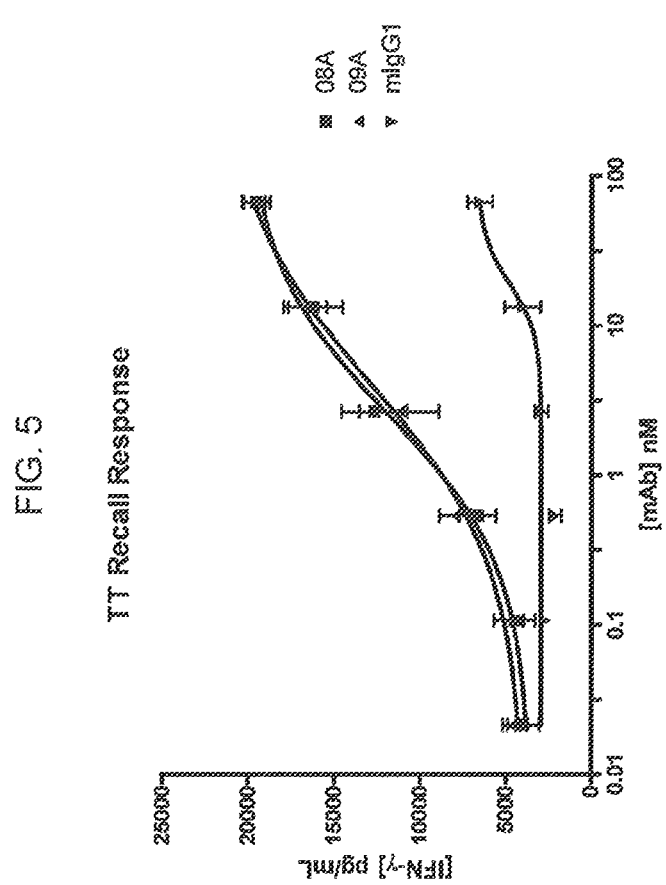
FIG. 5 shows results of experiments demonstrating that anti-PD-1 antibodies promote T cell proliferation and cytokine secretion (IL-2 and IFNγ) when stimulated with the recall antigen tetanus toxoid.

Human Recall T Cell Response to TT Challenge is Enhanced by hPD-1.08A and hPD-1.09A Another assay used to profile the functional effect of anti-human PD-1 antibodies blocking receptor interaction with its natural ligands used the tetanus toxoid (TT) antigen to stimulate pre-existing memory T cells in healthy donor blood. To this end, freshly prepared PBMC ($2\times10^5$ cells) were plated in 96 well round-bottom plates in complete RPMI 1640 medium (containing 5% heat inactivated human serum), pre-incubated with test antibodies at varying concentration and stimulated with TT (Astarte Biologics) at a concentration of 100 ng/mL. The cells were incubated for 3-7 days at 37° C., 5% $CO_2$ after which supernatants were harvested. Cytokine concentrations were determined by ELISA (IL-2 and IFN-γ ELISA detection antibody pair sets from eBioscience) and multiplex analysis (Luminex platform—Biosource cytokine detection kits). Blockade of PD-1 enhanced proliferation and significantly enhanced cytokine production (FIG. 5) including IFNγ and IL-2 compared to antigen alone. Luminex analysis revealed that production of the cytokines GM-CSF, RANTES, and IL-6 are increased upon PD-1 blockage.

Staining of Human PD-1 on Formalin-Fixed Paraffin-Embedded Human Cells

Since SEB-stimulated blood cells demonstrated enhanced expression of PD-1 by flow cytometry, these cells were used to determine if hPD-1.09A could detect PD-1 in formalin-fixed paraffin embedded tissue for histological use. Human donor peripheral blood mononuclear cells were stimulated with 0.1 µg/mL SEB for 3 days, after which the non-adherent cells (mainly lymphocytes) were collected, washed twice with PBS and centrifuged (1100 rpm for 5 min.). The cells were fixed for 10 min in 4% formaldehyde, the cell-pellet was embedded in agarose, dehydrated in ethanol (subsequently 70%, 80%, 96% and 100%) and xylene, and thereafter embedded in paraffin. Sections (4 µm) were mounted onto glass slides and hydrated (xylene, ethanol 100%, 96%, 80%, 70%, PBS buffer), after which antigen retrieval in heated citrate buffer was performed using standard methodology. Peroxidase activity was blocked using 100% methanol including 0.3% $H_2O_2$ and slides were rinsed in water and PBS, Tween 0.1%. Sections were incubated with hPD-1.09A for 1.5 hours at room temperature, rinsed with PBS-Tween, followed by standard detection methods. Slides were counterstained with hematoxylin for 30 seconds at room temperature, dehydrated with xylene, and mounted for microscopical examination. These experiments showed that lymphocytes derived from SEB stimulated PBMC cultures stained strongly (when compared to the isotype control) with hPD-1.09A, as opposed to unstimulated PBMC cultures, indicating that hPD-1.09A is useful as a diagnostic reagent.

Example 4: Anti-PD-1 Antibodies Sequences and Subsequent Humanization

Cloning of Immunoglobulin cDNAs

Using degenerate primer PCR-based methods, the DNA sequences encoding the variable regions of the mouse antibodies expressed by hybridomas hPD-1.08A and hPD-1.09A were determined. Briefly, gene specific cDNAs for the heavy and light chains were generated using the iScript Select cDNA synthesis kit (Biorad #1708896) according to the manufacturer's instructions. PCR primers used were based on the Ig-primer set (Novagen #69831-3). Degenerate PCR reactions were carried out using Taq polymerase according to the Novagen primer set protocol. PCR products were analyzed by agarose gel electrophoresis. The expected amplicon size for both the heavy and light chain variable region is about 500 base pairs. Two µl of Taq-amplified PCR product from reactions which yielded an appropriate band were cloned into the pCR4 TOPO vector (Invitrogen #K4595-40) and transformed into DH5-alpha E. coli as directed by the manufacturer. Clones were screened by colony PCR using universal M13 forward and reverse primers and two to three clones from each reaction were chosen for DNA sequencing analysis.

Clones were sequenced in both directions using universal primers M13 forward, M13 reverse, T3 and T7. Results of each sequencing reaction for each clone were analyzed using Seqman. Consensus sequences were searched against databases of germline and rearranged Ig Variable region sequences using NCBI Ig-Blast (http://www.ncbi.nlm.nih.gov/projects/igblast/). Blast results for hPD-1.08A identified a productively (in-frame) rearranged heavy chain with no stop codons introduced. Light chain clones were identified which encode two different sequences; one is a productively (in-frame) rearranged light chain with no stop codons introduced, the other is a non-productively rearranged sequence containing a frame-shift leading to a stop codon in the FR4 region. The non-productive sterile transcript observed likely originates from the myeloma fusion partner (Carroll W. L. et al., *Mol. Immunol.* 25:991-995 (1988) and was ruled out.

Blast results for hPD-1.09A identified productively (in-frame) rearranged heavy and light chains with no stop codons introduced. The amino acid sequences of the expressed proteins were been confirmed by mass spectrometry. The sequences are disclosed in the attached Sequence Listing and listed in table IV.

TABLE IV

Sequence ID numbers for murine anti-human PD-1 antibodies of this invention

| SEQ ID NO: | Description |
|---|---|
| 1 | hPD-1.08A heavy chain variable region (DNA) |
| 2 | hPD-1.08A light chain variable region (DNA) |
| 3 | hPD-1.09A heavy chain variable region (DNA) |
| 4 | hPD-1.09A light chain variable region (DNA) |
| 5 | hPD-1.08A heavy chain variable region (AA) |
| 6 | hPD-1.08A light chain variable region (AA) |
| 7 | hPD-1.09A heavy chain variable region (AA) |
| 8 | hPD-1.09A light chain variable region (AA) |
| 9 | hPD-1.08A light chain CDR1 (AA) |
| 10 | hPD-1.08A light chain CDR2 (AA) |
| 11 | hPD-1.08A light chain CDR3 (AA) |
| 12 | hPD-1.08A heavy chain CDR1 (AA) |
| 13 | hPD-1.08A heavy chain CDR2 (AA) |
| 14 | hPD-1.08A heavy chain CDR3 (AA) |
| 15 | hPD-1.09A light chain CDR1 (AA) |
| 16 | hPD-1.09A light chain CDR2 (AA) |
| 17 | hPD-1.09A light chain CDR3 (AA) |
| 18 | hPD-1.09A heavy chain CDR1 (AA) |
| 19 | hPD-1.09A heavy chain CDR2 (AA) |
| 20 | hPD-1.09A heavy chain CDR3 (AA) |
| 21 | 109A-H heavy chain variable region (DNA) |
| 22 | Codon optimized 109A-H heavy chain variable region (DNA) |
| 23 | Codon optimized 409A-H heavy chain full length (DNA) |
| 24 | K09A-L-11 light chain variable region (DNA) |
| 25 | K09A-L-16 light chain variable region (DNA) |
| 26 | K09A-L-17 light chain variable region (DNA) |
| 27 | Codon optimized K09A-L-11 light chain variable region (DNA) |
| 28 | Codon optimized K09A-L-16 light chain variable region (DNA) |
| 29 | Codon optimized K09A-L-17 light chain variable region (DNA) |
| 30 | 109A-H heavy chain variable region (AA) |
| 31 | 409A-H heavy chain full length (AA) |
| 32 | K09A-L-11 light chain variable region (AA) |
| 33 | K09A-L-16 light chain variable region (AA) |
| 34 | K09A-L-17 light chain variable region (AA) |
| 35 | 109A-H heavy chain full length (AA) |
| 36 | K09A-L-11 light chain full length (AA) |
| 37 | K09A-L-16 light chain full length (AA) |
| 38 | K09A-L-17 light chain full length (AA) |

CDR and framework regions are annotated according to Kabat E. A., et al., 1991, Sequences of proteins of Immunological interest, In: *NIH Publication No.* 91-3242, US Department of Health and Human Services, Bethesda, Md.

Construction and Expression of Chimeric c109A Antibody

Chimeric light and heavy chains were constructed by linking the PCR-cloned cDNAs of mouse hPD-1.09A VL and VH regions to human kappa and IgG1 constant regions, respectively. The 5' and 3' ends of the mouse cDNA sequences were modified using PCR primers designed to add a suitable leader sequence to each chain, and restriction sites to enable cloning into existing recombinant antibody expression vectors.

COS-7 cells (0.7 mL at $10^7$/mL) were electroporated with 10 µg of each of the chimeric heavy and light chain expression plasmids. These cells were then cultured in 8 mL growth medium for three days. A sandwich ELISA was used to measure the antibody concentrations in the supernatants from the COS-7 transfections. This showed that the transfected COS-7 cells secreted about 295 ng/mL of the chimeric $IgG_1$-kappa antibody in three separate transfections.

Binding of the chimeric antibody produced by the transfected COS-7 cells was measured using PD-1 binding ELISA and CELISA (see Example 2) and was shown to bind to PD-1 with comparable affinity to that of the murine antibody.

Humanized Antibody Design

The hPD-1.09A antibody was humanized by MRCT (Cambridge UK) using CDR grafting technology (see, e.g., U.S. Pat. No. 5,225,539). Briefly, the variable chain sequences of the murine antibody hPD-1.09A were compared to those available in the Research Collaboratory for Structural Bioinforrnatics (RCSB) protein databank. A homology model of hPD-1.09A was generated based on the nearest VH and VK structures. Human sequences with highest identity to hPD-1.09A were identified and analyzed. (Foote and Winter, *J. Mol. Biol.* 224:487-499 (1992); Morea V. et al., *Methods* 20:267-279 (2000); Chothia C. et al., *J. Mol. Biol.* 186:651-663 (1985).) The most appropriate human frameworks on which to build the CDR grafted heavy and light chains were identified.

For the heavy chain, the framework encoded by genbank accession #AB063829 was determined to be the most appropriate. Analysis of the hPD-1.09A VK sequence shows that its CDR1 length (15 residues) is not found in any human VK. For this reason, frameworks of three different CDR1 lengths (11, 16 and 17 residues) were analyzed in order to test which CDR1 length would reproduce the behavior of hPD-1.09A VK. The human VK sequences with highest identity to hPD-1.09A VK at selected residues important in the structure and with CDR1 lengths 11, 16 and 17 were identified. The framework of genbank accession #M29469 was selected on which to base K109A-L-11. The framework from genbank accession #AB064135 was selected on which to base K09A-L-16 and the framework from genbank accession #X72431 was chosen on which to base K09A-L-17.

Straight grafts were performed to generate expression constructs for each chain. The DNA and protein sequences of 109A-H, K09A-L-11, K09A-L-16 and K09A-L-17 are disclosed in the attached Sequence Listing (Table IV).

An IgG4 version of the humanized h109A antibody was produced, with the stabilizing Adair mutation (Angal S. et al., *Mol. Immuol.* 30:105-108 (1993)), where serine 241 (Kabat numbering) is converted to proline. This sequence is disclosed in SEQ ID NOS: 23 and 31.

Example 5: Binding Characteristics and Functional Properties of Humanized Anti-PD-1 Antibodies Production and Purification Humanized antibodies h409A11, h409A16 and h409A17 were produced by transient transfection of CHO—S cells. Cells were grown in CD-CHO (Gibco) and C5467 media (Sigma) for 8 days in shaker flasks. Antibodies were purified from cell supernatants by Protein A chromatography, washed, eluted using 1 M acetic acid and neutralized using 3 M Tris. Finally, the buffer was exchanged for 100 mM acetic acid which had been adjusted to pH 5.5 with 1 M Tris base.

Binding and Kinetic Analysis

Protein-based and cell-based ELISAs to determine apparent binding affinities (reported as EC50 values) were performed as described in Example 2. The humanized anti-PD-1 antibodies each bound to PD-1/Fc and cellularly expressed PD-1 with comparable EC50 values to the murine parent antibody (Table V).

Figure 6:
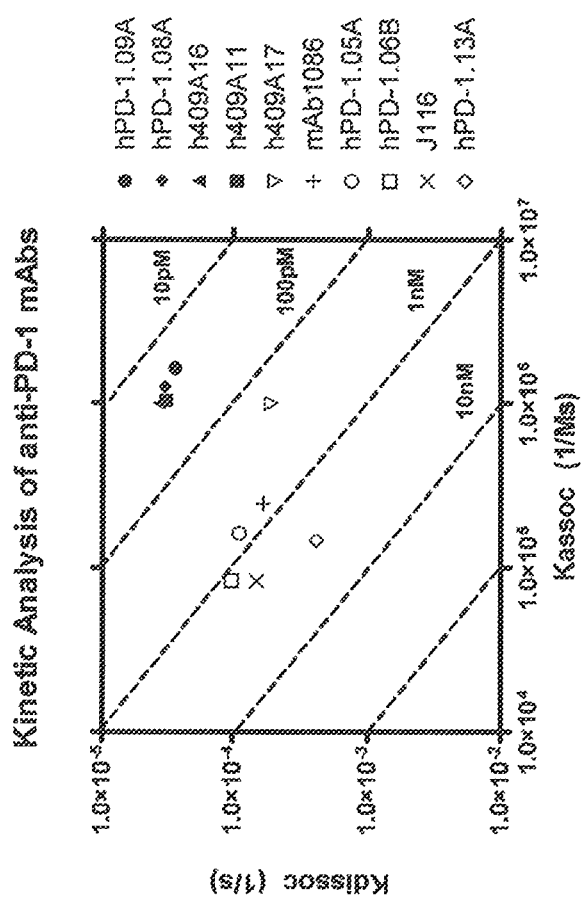
FIG. 6 is a graph depicting the $k_{assoc}$ and $k_{dissoc}$ rates for anti-PD-1 antibodies as measured by bio-light interferometry. Diagonal lines indicate theoretical calculated $K_D$ values. The antibodies are listed at the right by $K_D$ in ascending order.

Kinetic binding characteristics of the antibodies were also performed using bio-light interferometry as described in Example 2 (FIG. 6). Two of the humanized antibodies, h409A11 and h409A16, bound considerably more tightly than any other mAb tested using this assay, with $K_D$ determined to be 29 and 27 pM for h409A11 and h409A16, respectively (Table V). Compared to the other anti-PD-1 antibodies tested, the increased affinity is mainly due to a slower off-rate. Similar to the murine parental antibodies, the humanized anti-PD-1 antibodies h409A11, h409A16 demonstrated binding to cynomolgous PD-1 with $K_D$ determined to be below 120 pM.

Ligand Blockade

The ability of the humanized antibodies to block the binding of PD-L1 and PD-L2 to PD-1 was measured using a homogeneous competition assay and detection using an FMAT competition assay as described in Example 2.

Binding of both hPD-L1/Fc and hPD-L2/Fc to CHO-hPD-1 cells can be completely inhibited in a dose-dependent fashion by any of the humanized antibodies tested. Calculated $IC_{50}$ data are summarized in Table V. Similarly to the parent murine antibody hPD-1.09A, each of the humanized mAbs, h409A11, h409A16 and h409A17 inhibited PD-L1 and PD-L2 binding with $IC_{50}$ values below 1 nM. Similar to the murine parental antibodies, the humanized anti-PD-1 antibodies h409A11, h409A16 and h409A17 demonstrated inhibition of ligand binding to cynomolgous PD-1 with calculated $IC_{50}$ values under about 1 nM.

TABLE V

Binding characteristics of humanized anti-hPD-1 antibodies of the invention

| | Binding Analysis | | Ligand Blockade | | Kinetic Analysis | | |
|---|---|---|---|---|---|---|---|
| | ELISA | CELISA | FMAT | | Fortebio Octet | | |
| | EC50 (pM) | EC50 (pM) | IC50 (pM) | | $k_{assoc}$ | $k_{dissoc}$ | $K_D$ |
| mAb | hPD-1/Fc | hPD-1/CHO | PD-L1 | PD-L2 | 1/s | 1/Ms | M |
| h409A11 | 76 | 62 | 625 | 695 | 1.04E+06 | 3.05E−05 | 2.93E−11 |
| h409A16 | 90 | 63 | 696 | 810 | 9.97E+05 | 2.72E−05 | 2.73E−11 |
| h409A17 | 88 | 83 | 818 | 463 | 1.00E+06 | 1.91E−04 | 1.91E−10 |

Human T Cell Response to SEB is Enhanced by Humanized mAbs

Figure 7:
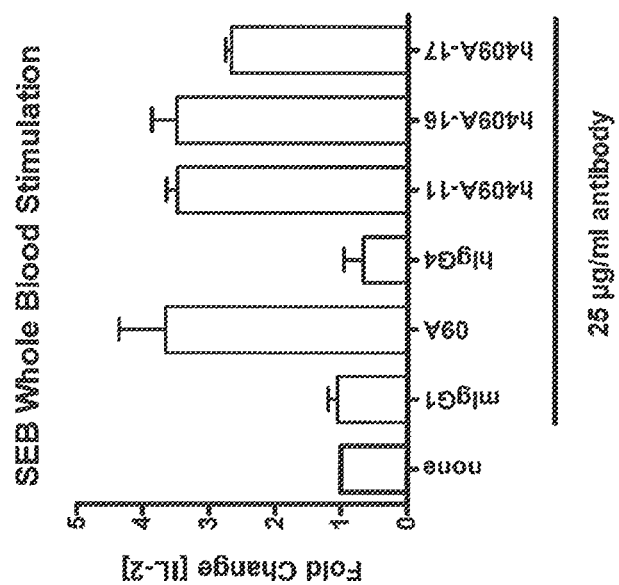
FIG. 7 is a bar graph which shows results of experiments demonstrating that SEB-stimulated IL-2 production by healthy donor blood cells is increased in the presence of 25 ug/ml murine (09A) or humanized anti-PD-1 antibodies (h409A11, h409A16 and h409A17). Bars show the average fold increase in IL-2 across three donors (+SEM). Mouse (m) IgG1 is the isotype control for anti-PD-1.09A (09A). Human (h) IgG4 is the isotype control for h409A11, h409A16 and h409A17 antibodies. Each IL-2 value is compared to its own control to determine the fold change. None=SEB alone.

Humanized anti-PD-1 antibodies were tested for their capacity to enhance T cell activity in vitro using blood cells from healthy volunteers as described in Example 3. Supernatants were collected after 4 days of culture and the amount of IL-2 produced was quantified using ELISA The humanized PD-1 antibodies demonstrated the capacity to increase IL-2 production stimulated by SEB (FIG. 7). Additionally, the humanized PD-1 antibodies increased SEB induced IL-2 production in cancer patient blood, similar to what is described in Example 3.

In summary, the humanized mAbs h409A11, h409A16, and h409A17 retained all functional activity during the humanization process. The h409A11 and h409A16 mAbs fully retained the affinity of the mouse parental antibody hPD109A upon humanization.

We claim:

1. A method of increasing the activity of an immune cell, comprising contacting the immune cell with a monoclonal antibody which binds to human programmed death receptor 1 (hPD-1), wherein the antibody blocks the binding of human PD-L1 and human PD-L2 to hPD-1 and comprises:
   a. three light chain CDRs having the amino acid sequences set forth in SEQ ID NOs: 15, 16 and 17 and
   b. three heavy chain CDRs having the amino acid sequences set forth in SEQ ID NOs: 18, 19 and 20.

2. A method of increasing the activity of an immune cell for the treatment of cancer in a human patient in need thereof, comprising administering to the patient a therapeutically effective amount of a monoclonal antibody which binds to human programmed death receptor 1 (hPD-1), wherein the antibody blocks the binding of human PD-L1 and human PD-L2 to hPD-1 and comprises:
   a. three light chain CDRs having the amino acid sequences set forth in SEQ ID Nos: 15, 16 and 17 and
   b. three heavy chain CDRs having the amino acid sequences set forth in SEQ ID Nos: 18, 19 and 20.

3. The method of claim 2, wherein the cancer is melanoma, renal cancer, prostate cancer, breast cancer, colon cancer, lung cancer, esophageal cancer, squamous cell carcinoma of the head and neck, liver cancer, ovarian cancer, cervical cancer, thyroid cancer, glioblastoma, or lymphoma.

4. The method of claim 3, wherein the cancer is melanoma, non-small cell lung cancer, or squamous cell carcinoma of the head and neck.

5. The method of claim 2, wherein the antibody is used in combination with an anti-neoplastic agent or immunogenic agent.

6. The method of claim 2, wherein the antibody is used in combination with chemotherapy, radiotherapy, or surgery.

7. The method of claim 2, wherein the antibody is used in combination with an antibody that binds to VEGF.

8. The method of claim 2, wherein the antibody is used in combination with an antibody that binds to EGFR.

9. The method of claim 2, wherein the antibody is used in combination with an antibody that binds to Her2/neu.

10. The method of claim 2, wherein the antibody is used in combination with an antibody that binds to a VEGF receptor.

11. The method of claim 2, wherein the antibody is used in combination with an antibody that binds to CTLA-4.

12. The method of claim 2, wherein the antibody is used in combination with an antibody that binds to OX-40.

13. The method of claim 2, wherein the antibody is used in combination with an antibody that binds to 4-1BB.

14. The method of claim 2, wherein the antibody is used in combination with an antibody that binds to ICOS.

15. The method of claim 2, wherein the antibody is used in combination with an antibody that binds to CD20.

16. The method of claim 2, wherein the antibody is used in combination with an antibody that binds to CD40.

17. The method of claim 2, wherein the antibody blocks binding of human PD-L1 and human PD-L2 to human PD-1 with an IC50 of about 1 nM or lower, wherein the IC50 is measured using an FMAT competition assay.

18. The method of claim 2, wherein the antibody binds PD-1 with a $K_D$ of about 30 pM or lower, wherein the binding is determined using bio-light interferometry.

19. The method of claim 2, wherein the antibody is an IgG4 isotype.

20. The method of claim 2, wherein the wherein the antibody is a human antibody, a humanized antibody or a chimeric antibody.

21. The method of claim 2, wherein the antibody blocks binding of human PD-L1 and human PD-L2 to human PD-1 with an IC50 of about 1 nM or lower, wherein the IC50 is measured using a FACS assay.

22. The method of claim 2, wherein the antibody comprises a light chain variable region comprising amino acid residues 20 to 130 of SEQ ID NO:32 and a heavy chain variable region comprising amino acid residues 20 to 139 of SEQ ID NO:30.

23. The method of claim 22, wherein the cancer is melanoma, renal cancer, prostate cancer, breast cancer, colon cancer, lung cancer, esophageal cancer, squamous cell carcinoma of the head and neck, liver cancer, ovarian cancer, cervical cancer, thyroid cancer, glioblastoma, or lymphoma.

24. The method of claim 23, wherein the cancer is melanoma, non-small cell lung cancer, or squamous cell carcinoma of the head and neck.

25. The method of claim 22, wherein the antibody is used in combination with an anti-neoplastic agent or immunogenic agent.

26. The method of claim 22, wherein the antibody is used in combination with chemotherapy, radiotherapy, or surgery.

27. The method of claim 22, wherein the antibody is used in combination with an antibody that binds to VEGF.

28. The method of claim 22, wherein the antibody is used in combination with an antibody that binds to EGFR.

29. The method of claim 22, wherein the antibody is used in combination with an antibody that binds to Her2/neu.

30. The method of claim 22, wherein the antibody is used in combination with an antibody that binds to a VEGF receptor.

31. The method of claim 22, wherein the antibody is used in combination with an antibody that binds to CTLA-4.

32. The method of claim 22, wherein the antibody is used in combination with an antibody that binds to OX-40.

33. The method of claim 22, wherein the antibody is used in combination with an antibody that binds to 4-1BB.

34. The method of claim 22, wherein the antibody is used in combination with an antibody that binds to ICOS.

35. The method of claim 22, wherein the antibody is used in combination with an antibody that binds to CD20.

36. The method of claim 22, wherein the antibody is used in combination with an antibody that binds to CD40.

37. The method of claim 22, wherein the antibody blocks binding of human PD-L1 and human PD-L2 to human PD-1 with an IC50 of about 1 nM or lower, wherein the IC50 is measured using an FMAT competition assay.

38. The method of claim 22, wherein the antibody binds PD-1 with a $K_D$ of about 30 pM or lower, wherein the binding is determined using bio-light interferometry.

39. The method of claim 22, wherein the antibody is an IgG4 isotype.

40. The method of claim 22, wherein the wherein the antibody is a human antibody, a humanized antibody or a chimeric antibody.

41. The method of claim 22, wherein the antibody comprises a light chain comprising amino acid residues 20 to 237 of SEQ ID NO:36 and a heavy chain comprising amino acid residues 20 to 466 of SEQ ID NO:31.

42. The method of claim 41, wherein the cancer is melanoma, renal cancer, prostate cancer, breast cancer, colon cancer, lung cancer, esophageal cancer, squamous cell carcinoma of the head and neck, liver cancer, ovarian cancer, cervical cancer, thyroid cancer, glioblastoma, or lymphoma.

43. The method of claim 42, wherein the cancer is melanoma, non-small cell lung cancer, or squamous cell carcinoma of the head and neck.

44. The method of claim 41, wherein the antibody is used in combination with an anti-neoplastic agent or immunogenic agent.

45. The method of claim 41, wherein the antibody is used in combination with chemotherapy, radiotherapy, or surgery.

46. The method of claim 41, wherein the antibody is used in combination with an antibody that binds to VEGF.

47. The method of claim 41, wherein the antibody is used in combination with an antibody that binds to EGFR.

48. The method of claim 41, wherein the antibody is used in combination with an antibody that binds to Her2/neu.

49. The method of claim 41, wherein the antibody is used in combination with an antibody that binds to a VEGF receptor.

50. The method of claim 41, wherein the antibody is used in combination with an antibody that binds to CTLA-4.

51. The method of claim 41, wherein the antibody is used in combination with an antibody that binds to OX-40.

52. The method of claim 41, wherein the antibody is used in combination with an antibody that binds to 4-1BB.

53. The method of claim 41, wherein the antibody is used in combination with an antibody that binds to ICOS.

54. The method of claim 41, wherein the antibody is used in combination with an antibody that binds to CD20.

55. The method of claim 41, wherein the antibody is used in combination with an antibody that binds to CD40.

56. The method of claim 41, wherein the antibody blocks binding of human PD-L1 and human PD-L2 to human PD-1 with an IC50 of about 1 nM or lower, wherein the IC50 is measured using an FMAT competition assay.

57. The method of claim 41, wherein the antibody binds PD-1 with a $K_D$ of about 30 pM or lower, wherein the binding is determined using bio-light interferometry.

* * * * *

UNITED STATES PATENT AND TRADEMARK OFFICE
CERTIFICATE OF CORRECTION

PATENT NO. : 11,117,961 B2
APPLICATION NO. : 15/810892
DATED : September 14, 2021
INVENTOR(S) : Gregory John Carven, Hans van Eenennaam and Gradus Johannes Dulos It is certified that error appears in the above-identified patent and that said Letters Patent is hereby corrected as shown below:

On the Title Page

In item (60) replace:
"Division of application No. 14/576,448, filed on Dec. 19, 2014, now Pat. No. 9,834,605, which is a division of application No. 13/719,756, filed on Dec. 19, 2012, now Pat. No. 8,952,136, which is a continuation of application No. 12/663,950, filed as application No. PCT/US2008/007463 on Jun. 13, 2008, now Pat. No. 8,354,509."
With:
"Division of application No. 14/576,448, filed on Dec. 19, 2014, now Pat. No. 9,834,605, which is a division of application No. 13/719,756, filed on Dec. 19, 2012, now Pat. No. 8,952,136, which is a division of application No. 12/663,950, filed as application No. PCT/US2008/007463 on Jun. 13, 2008, now Pat. No. 8,354,509."

Signed and Sealed this
Thirteenth Day of February, 2024

Katherine Kelly Vidal
*Director of the United States Patent and Trademark Office*